(12) United States Patent
Wilson et al.

(10) Patent No.: US 12,370,180 B2
(45) Date of Patent: Jul. 29, 2025

(54) P38 MAP KINASE INHIBITORS FOR TREATING FRIEDREICH'S ATAXIA

(71) Applicant: THE TRUSTEES OF THE UNIVERSITY OF PENNYSLVANIA, Philadelphia, PA (US)

(72) Inventors: Robert B. Wilson, Wynnewood, PA (US); Maria Grazia Cotticell, Philadelphia, PA (US); Yongping Wang, Wynnewood, PA (US); Shujuan Xia, Media, PA (US); Avinash Kaur, Philadelphia, PA (US); John W. Tobias, Wynnewood, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/561,390

(22) PCT Filed: Mar. 23, 2016

(86) PCT No.: PCT/US2016/023803
§ 371 (c)(1),
(2) Date: Sep. 25, 2017

(87) PCT Pub. No.: WO2016/154329
PCT Pub. Date: Sep. 29, 2016

(65) Prior Publication Data
US 2019/0083470 A1    Mar. 21, 2019

Related U.S. Application Data

(60) Provisional application No. 62/137,545, filed on Mar. 24, 2015.

(51) Int. Cl.
*A61K 31/437*    (2006.01)
*A61K 31/416*    (2006.01)
(Continued)

(52) U.S. Cl.
CPC .......... *A61K 31/437* (2013.01); *A61K 31/416* (2013.01); *A61K 31/4418* (2013.01);
(Continued)

(58) Field of Classification Search
CPC ................ A61K 31/437; A61K 31/416; A61K 31/4418; A61K 31/497; A61K 31/519; A61K 31/5377; A61P 25/28
See application file for complete search history.

(56) References Cited

U.S. PATENT DOCUMENTS

2010/0166737 A1    7/2010    Bernard-Pierott et al.

OTHER PUBLICATIONS

Fisk, Therapeutic Potential of p38 MAP Kinase Inhibition in the Management of Cardiovascular Disease, Am J Cardiovasc Drugs, 2014, 14, pp. 155-165 (Year: 2014).*
(Continued)

*Primary Examiner* — Savitha M Rao
*Assistant Examiner* — Andrew P Lee
(74) *Attorney, Agent, or Firm* — Mark S. Cohen; PEARL COHEN ZEDEK LATZER BARATZ LLP

(57) ABSTRACT

The invention provides p38 MAPK inhibitors that compensate for a frataxin deficiency or mutation and methods of using the same (e.g., to treat Friedreich's ataxia).

18 Claims, 17 Drawing Sheets
Specification includes a Sequence Listing.

A

B

C

D

(51) Int. Cl.
*A61K 31/4418* (2006.01)
*A61K 31/497* (2006.01)
*A61K 31/519* (2006.01)
*A61K 31/5377* (2006.01)
*A61P 25/28* (2006.01)

(52) U.S. Cl.
CPC .......... *A61K 31/497* (2013.01); *A61K 31/519* (2013.01); *A61K 31/5377* (2013.01); *A61P 25/28* (2018.01)

(56) References Cited

OTHER PUBLICATIONS

Garcia-Gimenez, Differential Expression of PGC-1α and Metabolic Sensors Suggest Age-Dependent Induction of Mitochondrial Biogenesis in Friedreich Ataxia Fibroblasts, PLoS ONE, 2011, 6(6), pp. 1-11 (Year: 2011).*

Lu et al. Frataxin deficiency induces Schwann cell Inflammation and death. Biochim Biophys-Acta Nov. 2009 vol. 1792 No. 11 pp. 1052-1061. Especially abstract, p. 1052 col. 2 para 1, p. 1058 col. 1 para 3; p. 1058 col. 2 para 1; p. 1059 fig 8B; p. 1059 fig 9.

* cited by examiner

Effectiveness of additional p38 inhibitors on the growth defect of primary FA fibroblasts
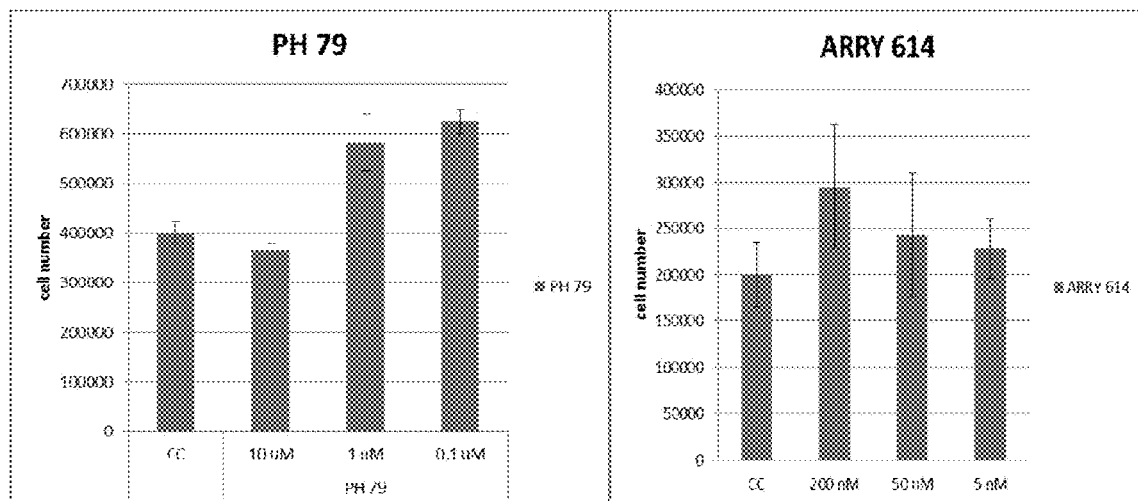
Figure 15A
Figure 15B
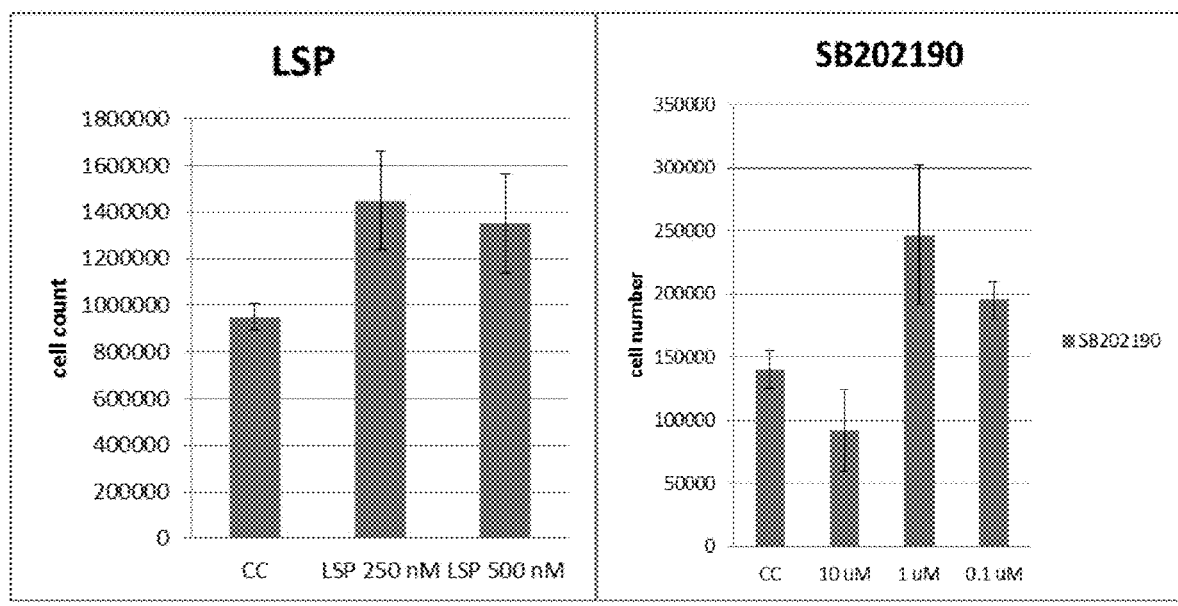
Figure 15C
Figure 15D

SEQUENCE LISTING

```
<160> NUMBER OF SEQ ID NOS: 10

<210> SEQ ID NO 1
<211> LENGTH: 64
<212> TYPE: DNA
<213> ORGANISM: Artificial Sequence
<220> FEATURE:
<223> OTHER INFORMATION: Vector Sequence of shRNA

<400> SEQUENCE: 1
gccaatcggg gaggtcggcg catatcatgc taaaccatga tatgcgccga cctcccgat      60 tggc                                                                  64

<210> SEQ ID NO 2
<211> LENGTH: 64
<212> TYPE: DNA
<213> ORGANISM: Artificial Sequence
<220> FEATURE:
<223> OTHER INFORMATION: Vector Sequence of shRNA

<400> SEQUENCE: 2
caacagaatg gaagagtgct gggtggtggc taaacccacc acccagcact cttccattct      60
gttg                                                                  64

<210> SEQ ID NO 3
<211> LENGTH: 27
<212> TYPE: RNA
<213> ORGANISM: Artificial Sequence
<220> FEATURE:
<223> OTHER INFORMATION: siRNA

<400> SEQUENCE: 3
```
aacagaaugg aagagugcug ggudgdg                                27

<210> SEQ ID NO 4
<211> LENGTH: 27
<212> TYPE: RNA
<213> ORGANISM: Artificial Sequence
<220> FEATURE:
<223> OTHER INFORMATION: siRNA

<400> SEQUENCE: 4
uguugucuua ccuucucacg acccacc                                27

<210> SEQ ID NO 5
<211> LENGTH: 27
<212> TYPE: RNA
<213> ORGANISM: Artificial Sequence
<220> FEATURE:
<223> OTHER INFORMATION: siRNA

<400> SEQUENCE: 5
aacacaaugg aagagugcug ggudgdg                                27

<210> SEQ ID NO 6
<211> LENGTH: 27
<212> TYPE: RNA
<213> ORGANISM: Artificial Sequence
<220> FEATURE:
<223> OTHER INFORMATION: siRNA

<400> SEQUENCE: 6
uguuguguua ccuucucacg acccacc                                27

<210> SEQ ID NO 7
<211> LENGTH: 27
<212> TYPE: RNA
<213> ORGANISM: Artificial Sequence
<220> FEATURE:
<223> OTHER INFORMATION: siRNA

<400> SEQUENCE: 7
aacagaaugg aagaguccug ggudgdg                                27

<210> SEQ ID NO 8
<211> LENGTH: 27
<212> TYPE: RNA
<213> ORGANISM: Artificial Sequence
<220> FEATURE:
<223> OTHER INFORMATION: siRNA

<400> SEQUENCE: 8
uguugucuua ccuucucagg acccacc                                27

<210> SEQ ID NO 9
<211> LENGTH: 64
<212> TYPE: DNA
<213> ORGANISM: Artificial Sequence
<220> FEATURE:
<223> OTHER INFORMATION: Vector Sequence of shRNA

<400> SEQUENCE: 9
gcccctcggg caggtcggcg aatatcatgc taaactatga tatgcgccga cctcccgat   60 tggc                                                          64

<210> SEQ ID NO 10

```
<211> LENGTH: 64
<212> TYPE: DNA
<213> ORGANISM: Artificial Sequence
<220> FEATURE:
<223> OTHER INFORMATION: Vector Sequence of shRNA

<400> SEQUENCE: 10
gcccctcggg caggtcggcg aatatcatgc taaactatga tatgcgccga ccttcccgat    60
tggc                                                                64
```

P38 MAP KINASE INHIBITORS FOR TREATING FRIEDREICH'S ATAXIA

CROSS-REFERENCES TO RELATED APPLICATIONS

This application is a National Phase Application of PCT International Application No. PCT/US16/23803, International Filing Date Mar. 23, 2016, claiming claims priority of U.S. Provisional Application 62/137,545, filed on Mar. 24, 2015, the disclosure of each of which is incorporated herein by reference.

GOVERNMENT INTEREST STATEMENT

This invention was made with government support under grant number GM090304 awarded by the National Institutes of Health. The government has certain rights in the invention.

FIELD OF THE INVENTION

Described herein are p38 mitogen-activated protein kinase (MAPK) inhibitors that compensate for a frataxin deficiency or mutation, and methods of using them (e.g., to treat Friedreich's ataxia).

BACKGROUND OF THE INVENTION

Mitochondrial dysfunction has been established to contribute to the pathology of numerous diseases and is suspected in many more. A role for loss of mitochondrial function in normal aging has long been suspected. Most hypotheses focus on free radical damage to mitochondrial DNA. Mitochondrial DNA (mtDNA) lies in close proximity to the mitochondrial respiratory chain, which produces free radicals even during normal respiration. Somatic mtDNA mutations accumulate with age in post-mitotic tissues in association with a decline in mitochondrial function. MtDNA mutations are propagated during the turnover of mitochondria, which have a limited lifespan of only a few weeks, even in post-mitotic cells. Because mtDNA contributes disproportionally to respiratory complexes I, III, and IV, these complexes are disproportionally affected when mtDNA is damaged. Disproportional effects on mitochondrial respiratory complexes increase the production of free radicals by impeding the normal flux of electrons through the electron transport chain; the increase in free radicals causes further damage to mtDNA, creating a vicious cycle. That the association between the accumulation of mtDNA mutations and aging is likely not an epiphenomenon is indicated by the striking premature aging phenotype of transgenic mice with an increased mtDNA mutation rate due to expression of a proof-reading-defective mitochondrial DNA polymerase.

Loss of mitochondrial function, particularly complex I function, likely contributes to Parkinson's disease (PD) as well. Complex I (NADH-ubiquinone oxidoreductase) activity is selectively decreased 15-30% in the substantia nigra (SN) in sporadic PD. 1-Methyl-4-phenyl-1,2,3,6-tetrahydropyridine (MPTP) is a neurotoxin that causes a parkinsonian syndrome in humans and mice: MPTP is metabolized in the brain to MPP+, a complex I inhibitor that accumulates in dopaminergic neurons. Chronic inhibition of complex I with rotenone, throughout the brain, causes selective degeneration of dopaminergic neurons in the SN. Rotenone-treated rats develop all the pathological hallmarks of PD, including distribution of pathology, nigrostriatal dopaminergic neurodegeneration, formation of Lewy-Body-like cytoplasmic inclusions, and oxidative damage. The hypokinesia in rats treated with rotenone may also reflect, at least in part, a general health problem rather than loss of nigrostriatal dopaminergic neurons.

A role for mitochondrial dysfunction in Friedreich's ataxia (FRDA or FA) is also recognized FRDA is an inherited disease that causes progressive damage to the nervous system and muscle cells resulting in symptoms ranging from uncoordination, gait disturbance, and speech problems to heart disease and muscle fatigueability. FRDA has a prevalence of approximately 1 in 40,000 in Caucasians. Symptoms of FRDA include progressive ataxia of all four limbs, dysarthria, areflexia, sensory loss, and exercise intolerance. Skeletal deformities and cardiomyopathy are found in most patients, impaired glucose tolerance and diabetes mellitus are found in ~30% of patients, and reduced visual acuity, including a pigmentary retinopathy, and hearing loss are occasionally seen. The neurological signs and symptoms are largely secondary to degeneration of the large sensory neurons of the dorsal root ganglia and spinocerebellar tracts. Symptoms usually begin between the ages of 5 and 15 but can, on rare occasions, appear as early as 18 months or as late as 50 years of age. The first symptom to appear is usually difficulty in walking, or gait ataxia. The ataxia gradually worsens and slowly spreads to the arms and then the trunk. Foot deformities such as clubfoot, flexion (involuntary bending) of the toes, hammer toes, or foot inversion (turning inward) may be early signs. Over time, muscles begin to atrophy, especially in the feet, lower legs, and hands, and deformities develop. Other symptoms include loss of deep tendon reflexes, especially in the knees and ankles. Generally, within 10 to 20 years after the appearance of the first symptoms, afflicted individuals are confined to a wheelchair, and in later stages of the disease become completely incapacitated. Life expectancy may be affected, and many people with FRDA die in adulthood from the associated heart disease: myocardial failure is the most common cause of premature death. There are currently no approved treatments for FRDA and the resultant disability, prolong the life of a Friedreich's ataxia patient, or cure the disorder.

Friedreich's ataxia is an autosomal recessive disease caused by a triplet (GAA) repeat expansion in the first intron of the frataxin (FXN) gene, which leads to decreased frataxin protein levels. Frataxin is found primarily in mitochondria where it chaperones iron for the formation of iron-sulfur clusters (ISCs) and may also act to store and detoxify excess iron. Iron-sulfur clusters are important prosthetic groups in the mitochondrial electron transport chain and other enzymes, including aconitase in the Krebs cycle and mitochondrial respiratory complexes I, II, and III. The decrease in frataxin function in Friedreich ataxia results in decreased ISC assembly; in Friedreich ataxia patients, as well as in yeast and mouse models, this is associated with mitochondrial dysfunction, mitochondrial iron accumulation, cytosolic iron depletion, and increased oxidative stress.

SUMMARY OF THE INVENTION

In one aspect, methods for treating a subject (e.g., a human) at risk for developing Friedreich's ataxia or suffering from Friedreich's ataxia or reducing the symptoms thereof are provided, the methods comprise: administering to the subject a therapeutically effective amount of a p38 mitogen-activated protein kinase (MAPK) inhibitor.

In another aspect, methods for compensating for a frataxin deficiency or mutation in a subject (e.g., a human) are provided, the methods comprise: administering to the subject a therapeutically effective amount of a p38 mitogen-activated protein kinase (MAPK) inhibitor.

In another aspect, methods for compensating for a frataxin deficiency or mutation in a cell are provided, the methods comprise, administering (e.g., in vitro, in vivo, or ex vivo) to the cell an effective amount of a p38 mitogen-activated protein kinase (MAPK) inhibitor.

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 9A shows the secretion of GM-CSF and VEGF; FIG. 9B shows the secretion of MCP-1, IL-8, IP-10, GRO, IL-6, and RANTES. These secretion patterns matched the expression changes seen on microarray analysis of mRNAs of the same cytokines.

FIGS. 15A-15D: Effect of additional p38 MAPK inhibitors (PH 79 [PH-797804]; ARRY 614 [ARRY-614; pexmetinib]; LSP [losmapimod; GW856553]; and SB-202190) on the growth defect of primary FA fibroblasts.

DETAILED DESCRIPTION OF THE INVENTION

Figure 1:
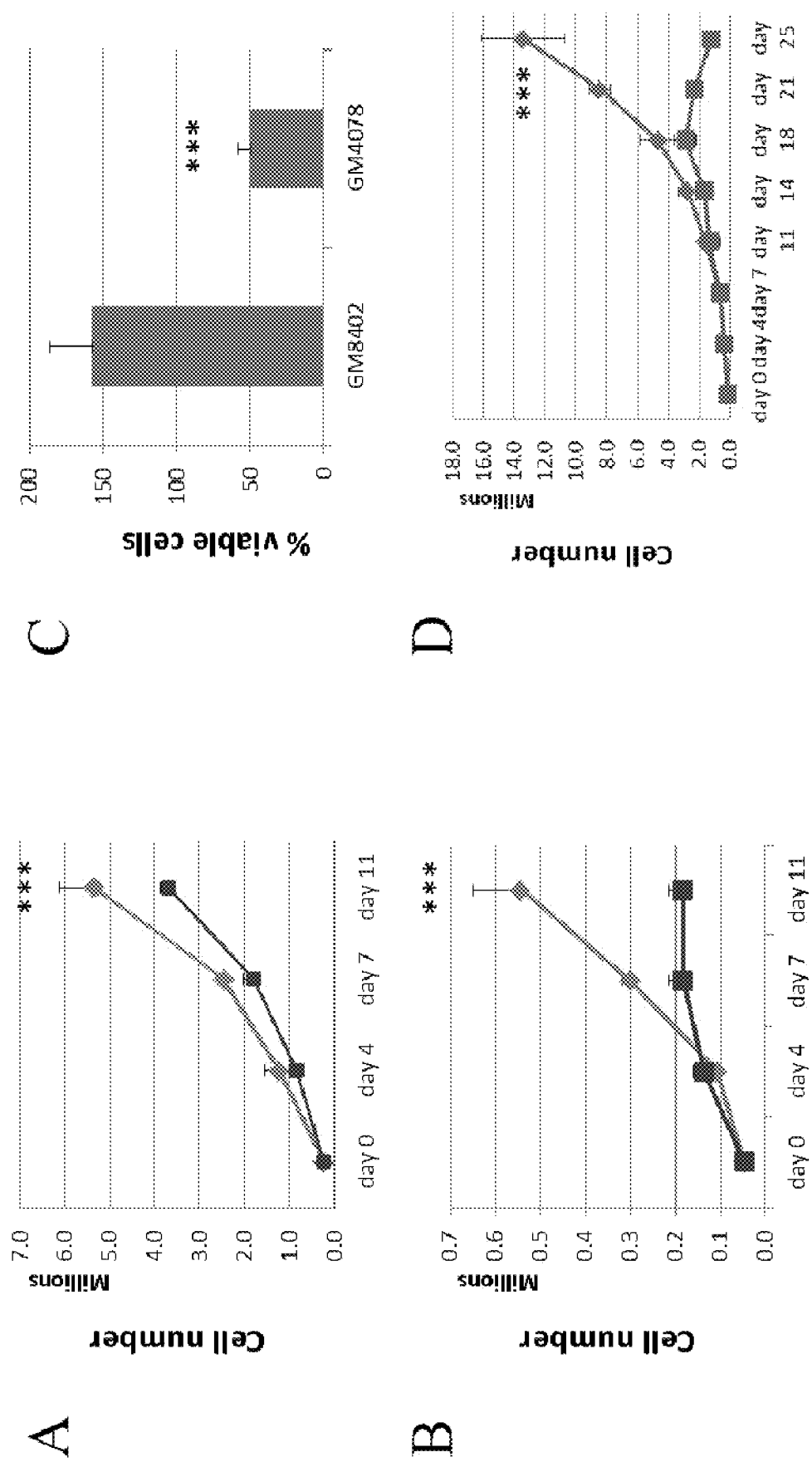
FIG. 1: Increased sensitivity of Friedreich's ataxia (FRDA) cells to (3-Hydroxybutyrate (BHB) medium. (A) Growth of normal control fibroblasts (GM8400) in BHB-based medium (squares) was slightly decreased compared to growth in regular, glucose-based medium (diamonds). Cells were kept sub-confluent. The data shown are the means of triplicate samples+/−one SD. *p<0.005. (B) Growth of primary FRDA fibroblasts (GM3816) in BHB-based medium (squares) was dramatically decreased, leading to growth arrest, compared to growth in regular, glucose-based medium (diamonds; see Materials and Methods). Cells were kept sub-confluent. The data shown are the means of triplicate samples+/−one SD. *p<0.005. (C) Survival of normal control fibroblasts (GM8402) and FA fibroblasts (GM4078) in DMEM plus BHB after 12 days in culture. *p<0.005. (D) Growth of primary FRDA fibroblasts with large GAA repeat expansions (GM3665B) in BHB-based medium (squares) was dramatically decreased, leading to growth arrest and some loss of viability, compared to growth in glucose-based medium (diamonds). Cells were seeded at 80,000 cells per 100 mm dish and were kept sub-confluent. The data shown are the means of triplicate samples+/−one SD. *p<0.005.

Friedreich's ataxia (FRDA or FA) is an autosomal recessive neurodegenerative disorder caused by mutations in the FXN gene, which encodes the protein frataxin, and for which there are no currently accepted treatments. It is the most common hereditary ataxia and causes progressive damage to the nervous system, particularly sensory neurons, resulting in symptoms ranging from ataxia, muscle fatigability, and speech problems to hypertrophic cardiomyopathy. Frataxin localizes to the mitochondrial matrix, where it chaperones iron for the assembly of iron-sulfur clusters that are then employed by a variety of respiratory and other enzymes.

Mitogen-activated protein kinases (MAPKs) are a family of serine/threonine protein kinases that mediate fundamental biological processes and cellular responses to external stress signals. Increased activity of MAPK, in particular p38 MAPK, and their involvement in the regulation of the synthesis of inflammation mediators at the level of transcription and translation, make them potential targets for anti-inflammatory therapeutics. Inhibitors targeting p38 MAPK pathways exhibit anti-inflammatory activity.

p38 is a major signal transducer responding to cellular stress stimuli such as cytokines. Because p38 MAPK regulates the production of TNF-α and IL-1, p38 inhibitors are expected to inhibit not only the production of pro-inflammatory cytokines, but also their actions, thereby interrupting the vicious cycle that often occurs in inflammatory and immunoresponsive diseases. Thus, p38 plays a key role in mediating cell survival, growth, differentiation, inflammation and innate immunity.

In one aspect, methods for treating a subject (e.g., a human) at risk for developing Friedreich's ataxia or suffering from Friedreich's ataxia or reducing the symptoms thereof are provided, the methods comprise: administering to the subject a therapeutically effective amount of a p38 mitogen-activated protein kinase (MAPK) inhibitor.

In another aspect, methods for compensating for a frataxin deficiency or mutation in a subject (e.g., a human) are provided, the methods comprise: administering to the subject a therapeutically effective amount of a p38 mitogen-activated protein kinase (MAPK) inhibitor.

In another aspect, methods for compensating for a frataxin deficiency or mutation in a cell are provided, the methods comprise, administering (e.g., in vitro, in vivo, or ex vivo) to the cell an effective amount of a p38 mitogen-activated protein kinase (MAPK) inhibitor.

In another aspect, methods for compensating for a frataxin deficiency or mutation in a cell are provided. In some embodiments, the methods comprise administering (e.g., in vitro, in vivo, or ex vivo) to the cell an effective amount of an RNA molecule described herein or pharmaceutical compositions thereof. In some embodiments, the methods comprise administering (e.g., in vitro, in vivo, or ex vivo) to the cell an effective amount of an expression vector described herein.

A "chemokine" is a small cytokine involved in the migration and activation of cells, including phagocytes and lymphocytes, and plays a role in inflammatory responses. Examples of chemokines include, but are not limited to IL8, RANTES, MDC, IP10, MIP1-alpha, and MIP-beta.

A "cytokine" is a protein made by a cell that affects the behavior of other cells through a "cytokine receptor" on the surface of the cells the cytokine effects. Examples of cytokines include, but are not limited to, IL6 (IL-6), IL8 (IL-8), GM-CSF, RANTES, IL1-beta (IL-1-beta), VEGF, MCP-1, IP10 (IP-10), and GRO, as well as IL1-alpha, TNF, IL12 (IL-12, p40), and IFN-gamma Inhibition of p38 reduces secretion of these cytokines depending on various factors, as discussed in Freund et al., *EMBO J.* 30:1536-1548 (2001).

In another aspect, methods for altering cytokine expression and/or secretion are provided. In another aspect, methods for altering cytokine expression are provided. In another aspect, methods for altering cytokine secretion are provided. In some embodiments, the methods comprise administering to the subject a therapeutically effective amount of a p38 mitogen-activated protein kinase (MAPK) inhibitor. In some embodiments, cytokines include, but are not limited to, IL6 (IL-6), IL8 (IL-8), GM-CSF, RANTES, IL1-beta (IL-1-beta), VEGF, MCP-1, IP10 (IP-10), and GRO, as well as IL1-alpha, TNF, IL12 (IL-12, p40), and IFN-gamma. In some embodiments, alteration of cytokine expression and/or secretion comprises a decrease in cytokine expression and/or secretion.

Expression or secretion of a chemokine, cytokine, receptor, marker, or other protein of interest may be measured, either directly or indirectly, using a wide range of methods known to those of ordinary kill in the art, including, but not limited to, protein assays, immunoprecipitation methods, enzyme-linked immunosorbent assays (ELISA), Western blotting and other types of direct or indirect immunoblotting, spectrophotometry or ultraviolet (UV) methods, various antibody methods, PCR, and the like. Alternatively, methods may be used to detect or measure, either directly or indirectly, the level or a nucleic acid, such as mRNA, the binding of a protein to a nucleic acid, the binding of a drug to a protein, and the like.

The phrase "the phenotype thereof" refers to an effect that is a partial, an equivalent, or in excess of the extent of the effect of the preceding term or terms. For example, frataxin depletion increases mitochondrial iron accumulation, increases oxidative stress and causes mitochondrial dysfunction. Mitochondrial dysfunction includes reduction or other alteration of the mitochondrial energy production (mitochondrial respiration) and oxidative stress pathway, defects in mitochondrial control, reduction in mitochondrial iron-sulfur clusters (ISC, Fe—S compounds/clusters), reduction in heme synthesis, reduction in mitochondrial production of adenosine triphosphate (ATP), increase in superoxide production, and alteration of apoptosis pathways. Increasing cellular frataxin gene expression results in a decrease in iron accumulation, a decrease in oxidative stress, or improving mitochondrial dysfunction. Thus, the phenotype of increasing frataxin gene expression can produce a partial decrease in iron accumulation, partial decrease in oxidative stress or partial reduction of mitochondrial dysfunction. Additionally, the phenotype of increasing frataxin gene expression can produce an extent of decrease in iron accumulation, decrease in oxidative stress or reduction of mitochondrial dysfunction equivalent to that extent achieved by increasing frataxin gene expression. Alternatively, the phenotype of increasing frataxin gene expression can produce an extent of decrease in iron accumulation, decrease in oxidative stress or reduction of mitochondrial dysfunction that exceeds that extent achieved by increasing frataxin gene expression.

The term "compensating" or "compensate" in reference to frataxin deficiency or mutation refers to the property of increasing, improving, or restoring cellular biochemistry or metabolism that is impaired by a frataxin deficiency or mutation, or the phenotype thereof, wherein the compensating may involve, but does not necessarily involve, or altogether does not involve, a direct effect on frataxin levels, expression or activity. In referring to RNA molecules embodied herein as compensating for a frataxin deficiency or mutation, the RNA molecules have the property in cells, tissues, or in subjects, of increasing, improving, or restoring cellular biochemistry or metabolism that is impaired by a frataxin deficiency or mutation, wherein the RNA molecules may involve, but do not necessarily involve, or altogether does not involve, a direct effect on frataxin levels, expression or activity.

The term "subject" as used herein can be any suitable mammal, including primates, such as monkeys and humans, horses, cows, cats, dogs, rabbits, and rodents such as rats and mice. In one embodiment, the mammal to be treated in the methods provided herein is a human.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

As used herein, the singular forms "a," "an," and "the" include plural references unless the context clearly dictates otherwise. For example, the term "a molecule" can also include a plurality of molecules.

The phrase, "pharmaceutically acceptable derivative," as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others prodrugs. A prodrug is a derivative of a compound, usually with significantly reduced pharmacological activity, which contains an additional moiety, which is susceptible to removal in vivo yielding the parent molecule as the pharmacologically active species. An example of a prodrug is an ester, which is cleaved in vivo to yield a compound of interest. Another example is an N-methyl derivative of a compound, which is susceptible to oxidative metabolism resulting in N-demethylation. Pro-drugs of a variety of compounds, and materials and methods for derivatizing the parent compounds to create the prodrugs, are known and may be adapted to the present invention.

As used herein, the terms "treat" and "treatment" and the like refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already with the disease or condition as well as those prone to having the disease or condition or those in which the disease or condition is to be prevented.

Inhibitors of p38 MAPK include, but are not limited to, ARRY-371797 (ARRY-797; Array BioPharma Inc.), ARRY-614 (pexmetinib; Array BioPharma Inc. or Selleckchem), AZD-7624 (AstraZeneca Plc), LY-2228820 (ralimetinib dimesylate; Eli Lilly and Co. or Selleckchem), LY-3007113 (Eli Lilly and Co.), FX005 (Flexion Therapeutics Inc.), GSK610677 (GlaxoSmithKline Plc), GW856553 (GW856553X; losmapimod; GlaxoSmithKline Plc or Selleckchem), SB-681323 (dilmapimod; GlaxoSmithKline Plc), KC706 (Kemia Inc.), UR-13870 (Palau Pharma S.A.), PF-03715455 (PF-3715455; Pfizer Inc.), VX-745 (Vertex Pharmaceuticals Inc. or Selleckchem), SCID-469 (talmapimod; Scios Inc.), PH-797804 (Pfizer or Selleckchem), VX-702 (Selleckchem), SB-202190 (FHPI; Selleckchem), SB-203580 (Selleckchem), SB-239063, BIRB-796 (doramapimod; Selleckchem), BMS-582949, and pamapimod.

It will be appreciated that p38 MAPK inhibitors described herein may be strong inhibitors of p38 MAPK. For example, the p38 MAPK inhibitor has a binding inhibitory activity ($IC_{50}$ value) for p38 MAPK of 1000 μM or less, 1000 nM or less, 100 nM or less, 10 nM or less, or especially 1 nM or less. In another example, the p38 MAPK inhibitor has a binding inhibitory activity ($IC_{50}$ value) for p38 MAPK of between 1000 μM and 1 nM, between 1000 μM and 10 nM, between 1000 μM and 100 nM, between 1000 μM and 1000 nM, between 1000 nM and 1 nM, between 1000 nM and 10 nM, between 1000 nM and 100 nM, between 100 nM and 10 nM, between 100 nM and 1 nM, or between 10 nM and 1 nM.

In some embodiments, the p38 MAPK inhibitors disclosed herein inhibit a p38 MAPK pathway by at least about 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more.

Embodied herein are compounds as described above and pharmaceutical compositions thereof. It will be appreciated that the compounds and compositions, according to the methods of the present invention, may be administered using any amount and any route of administration effective for the treatment of Friedreich's ataxia and/or where compensation of a frataxin deficiency or mutation has a therapeutically useful role. Thus, the expression "effective amount" as used herein, refers to compensation for a frataxin deficiency or mutation, when it refers to a compensation to exhibit a therapeutic effect, then "therapeutically effective amount" is used. The exact amount required will vary from subject to subject, depending on the species, age, and general condition of the subject, the particular therapeutic agent, its mode and/or route of administration, and the like. The p38 MAPK inhibitors are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the p38 MAPK inhibitors and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds and the pharmaceutical compositions may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, the pharmaceutical compositions of this invention administered orally or parenterally.

In some embodiments, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments of the present invention, the active ingredient is formulated in a capsule. In accordance with this embodiment, the compositions of the present invention comprise, in addition to the active compound and the inert carrier or diluent, a hard gelatin capsule.

In some embodiments, the pharmaceutical compositions are administered by intravenous, intra-arterial, subcutaneous or intra-muscular injection of a liquid preparation. Suitable liquid formulations include solutions, suspensions, dispersions, emulsions, oils and the like. In some embodiments, the pharmaceutical compositions are administered intravenously and are thus formulated in a form suitable for intravenous administration. In some embodiments, the pharmaceutical compositions are administered intra-arterially and are thus formulated in a form suitable for intra-arterial administration. In some embodiments, the pharmaceutical compositions are administered intra-muscularly and are thus formulated in a form suitable for intra-muscular administration.

In some embodiments, the pharmaceutical compositions are administered topically to body surfaces and are thus formulated in a form suitable for topical administration. Topical formulations include, in some embodiments, gels, ointments, creams, lotions, drops and the like.

In some embodiments, the pharmaceutical composition is administered as a suppository, for example a rectal suppository or a urethral suppository. In some embodiments, the pharmaceutical composition is administered by subcutaneous implantation of a pellet. In some embodiments, the pellet provides for controlled release of active agent over a period of time.

In some embodiments, the active compound is delivered in a vesicle, e.g., a liposome.

Pharmaceutically acceptable carriers include solvents, dispersion media, buffers, coatings, antibacterial and antifungal agents, wetting agents, preservatives, buffers, chelating agents, antioxidants, isotonic agents and absorption delaying agents.

Pharmaceutically acceptable carriers include, for example, water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

In other embodiments, carriers or diluents used in methods of the present invention include, but are not limited to, a gum, a starch (e.g., corn starch, pregeletanized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In some embodiments, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In some embodiments, the compositions further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HC1, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), antioxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In some embodiments, the pharmaceutical compositions provided herein are controlled-release compositions, i.e. compositions in which the active compound is released over a period of time after administration. Controlled- or sustained-release compositions include formulation in lipophilic depots (e.g., fatty acids, waxes, oils). Alternatively, the agent may be administered using intravenous infusion, an implantable osmotic pump, a transdermal patch, liposomes, or other modes of administration. In one embodiment, a pump may be used (see Langer R, Science 249: 1527-1533 (1990); Sefton, CRC Crit. Ref. Biomed. Eng. 14:201 (1987); Buchwald et al., Surgery 88:507 (1980); Saudek et al., N. Engl. J. Med. 321:574 (1989). In some embodiments, polymeric materials are used; e.g., in microspheres in or an implant. In yet some embodiments, a controlled release system is placed in proximity to the target cell, thus requiring only a fraction of the systemic dose (see, e.g., Goodson, in Medical Applications of Controlled Release, vol. 2, pp. 115-138 (1984); and Langer, supra. In some embodiments, the composition is an immediate-release composition, i.e. a composition in which of the active compound is released immediately after administration.

The compositions also include, in some embodiments, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

In some embodiments, the methods of the present invention comprise administering an active compound as the sole active ingredient. However, also encompassed within the scope of the present invention are methods for treating diseases and disorders that comprise administering the active compound in combination with one or more therapeutic agents appropriate for the disease or disorder that is being treated, as is known in the art.

All sequence citations, accession numbers, references, patents, patent applications, scientific publications or other documents cited are hereby incorporated by reference.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

EXAMPLES

The existing paradigm for the use of RNA interference (RNAi) in the development of small-RNA therapeutics is to interfere with the expression of a single gene using a short-hairpin-loop RNA (shRNA) or short-interfering RNA (siRNA). However, the most potent endogenous microRNAs (miRNAs), on which shRNAs and siRNAs are modeled, target hundreds of mRNAs simultaneously through "seed-sequence" matches of ~7 nucleotides. Unsurprisingly, therefore, small-RNA therapeutic initiatives based on targeting single mRNAs are complicated by off-target effects, which diminish therapeutic indices. To challenge the single-gene-targeting paradigm, the first shRNA-expressing libraries that are completely random at the nucleotide level were designed and synthesized. Using a pooled approach, 3 million shRNAs can be screened in a single tissue-culture dish, selecting for the desired phenotype and retrieving "hit" shRNA-encoding sequences by PCR. Because the libraries are completely random, the screens are unbiased; the cells tell us which shRNAs are most effective and least toxic. This approach can be combined with bioinformatic pattern matching to identify conventional chemical-compound therapeutic candidates, bypassing in vivo delivery issues. Many cell-culture disease models unsuitable for microtiter-plate formats are amenable to this approach, thus the potential impact of applications of the library is significant and extremely broad.

The reason that the problem of off-target effects is so prevalent in current siRNA therapeutic initiatives, which invariably target single genes, is because a seven-nucleotide "seed sequence" in the guide strands of processed siRNAs is sufficient to interfere, at least partially, with the expression of target mRNAs. A given seven-nucleotide sequence should occur, on average, every 16,384 nucleotides ($4^7$), which is ~366,000 times in the human genome (of ~$3\times10^9$ basepairs). Thus siRNAs, like their natural counterparts, miRNAs, are inherently promiscuous. Of course, designers of single-gene-targeting, siRNA therapeutics are working on ways to minimize off-target effects sufficiently to achieve acceptable therapeutic indices. How successful they will be remains to be seen. Regardless, however, the ability to target sets of genes is precisely what makes miRNAs so bioactive, and single-gene targeting fails to take advantage of this. This approach bypasses the problem of off-target effects, and harnesses the power of multi-gene targeting.

The other major problem in current siRNA therapeutic initiatives is in vivo delivery. These results demonstrate an approach by which this problem can be bypassed as well. The first-generation, random shRNA-expressing library of 300,000 clones was screened in primary cells from patients with the neuro- and cardio-degenerative disorder, Friedreich's ataxia (FA). Hit shRNA-encoding sequences that reverse a disease-associated phenotype were identified, either as shRNAs expressed from vectors, or as transfected siRNAs. Although the problem of in vivo delivery of siRNAs has been solved for some tissues (such as hepatocytes), the problem remains for most, including neurons and cardiomyocytes, which are affected in FA.

Using microarrays, the gene-expression profiles of primary FA cells expressing one of the hit shRNAs were compared to controls. ~350 genes were identified with statistically significant changes in expression and pathway analyses using various software packages were performed. An unexpected pathway altered by one hit shRNA was identified; a pathway confirmed biochemically. The Ingenuity pathway analysis software package identified "upstream regulators" that, when inhibited or activated, induce a similar pattern of gene expression to that induced by one hit shRNA. Two of these upstream regulators were a transcription factor, and a drug. Treatment of primary FA cells with the drug, as well as inhibition of the transcription factor using targeted siRNAs, completely recapitulated the hit-shRNA's reversal of the disease-associated-phenotype. The implications of the FA study are that, in addition to using random shRNA screening to identify siRNA therapeutic candidates, screening can be combined with bioinformatic pattern matching to identify conventional chemical-compound therapeutic candidates, to identify potential therapeutic target proteins, and to discover biochemical pathways that elucidate disease mechanisms and inform additional therapeutic target identification.

RNAi and the Hypothesis Underlying the Present Approach

In the canonical RNAi pathway, microRNA (miRNA) genes are transcribed into primary (pri-) miRNAs, which are processed into short, self-complementary RNA stem-loop structures called pre-miRNAs. Pre-miRNAs are then processed into mature miRNAs, which are double-stranded; one of the two strands (the "guide strand") is loaded onto the RNA-Induced Silencing Complex (RISC). The guide strand sits in a groove of one of the Argonaut (AGO) proteins. Base-pairing of guide strands with target mRNAs leads to mRNA cleavage and/or translational repression. Short-hairpin-loop RNAs (shRNAs) are essentially artificial pre-miRNAs; short-interfering RNAs (siRNAs) are essentially artificial mature miRNAs.

The hypothesis underlying the approach in this Example is that the best way to identify the most effective small-RNA therapeutics and biologic tools is to use a random, shRNA-expressing library and screen by phenotype. This hypothesis derives from three aspects of the growing knowledge of miRNA biology: First, miRNAs do not target single genes; rather, they target hundreds of genes simultaneously through "seed sequences" of approximately seven nucleotides near the 5' ends of their guide strand. Yet the premise of most small-RNA therapeutic initiatives is the targeting of a single gene; thus, it is unsurprising that "off-target effects" complicate these initiatives.

Second, there is evidence that miRNAs are not only able to interfere with gene expression (RNAi), but can also activate gene expression. The mechanisms underlying this "RNA activation" (or "RNAa") are currently unknown and are therefore even less predictable than RNAi.

Third, mRNAs, including those from transcribed pseudogenes, can regulate miRNAs, and therefore each other, through "competing endogenous RNA" (ceRNA) networks. For example, the mRNAs encoded by the tumor suppressor PTEN, and by its pseudogene PTENP1, share many of the same miRNA target sites, allowing a common set of miRNAs to interfere with the expression of both mRNAs simultaneously. One group has shown that an increase in PTENP1 mRNA titrates out the miRNAs that also target PTEN mRNA, leading to an increase in PTEN expression; likewise, a decrease in PTENP1 mRNA frees up the miRNAs that also target PTEN mRNA, leading to a decrease in PTEN expression. Thus, in addition to regulating the expression of many genes directly, through seed-sequence interactions, a single miRNA has the potential to regulate the expression of many additional genes indirectly, through networks of mRNA/miRNA interactions.

In summary, miRNAs typically target hundreds of genes simultaneously through approximately seven-nucleotide seed sequences, they may also activate gene expression, and they can potentially modulate gene expression indirectly through complex networks of mRNA/miRNA interactions. Current siRNA therapeutic initiatives, which are designed to target single genes, are complicated by these aspects of miRNA biology; the present approach takes advantage of them, as described below.

Random shRNA Selection

Figure 2:
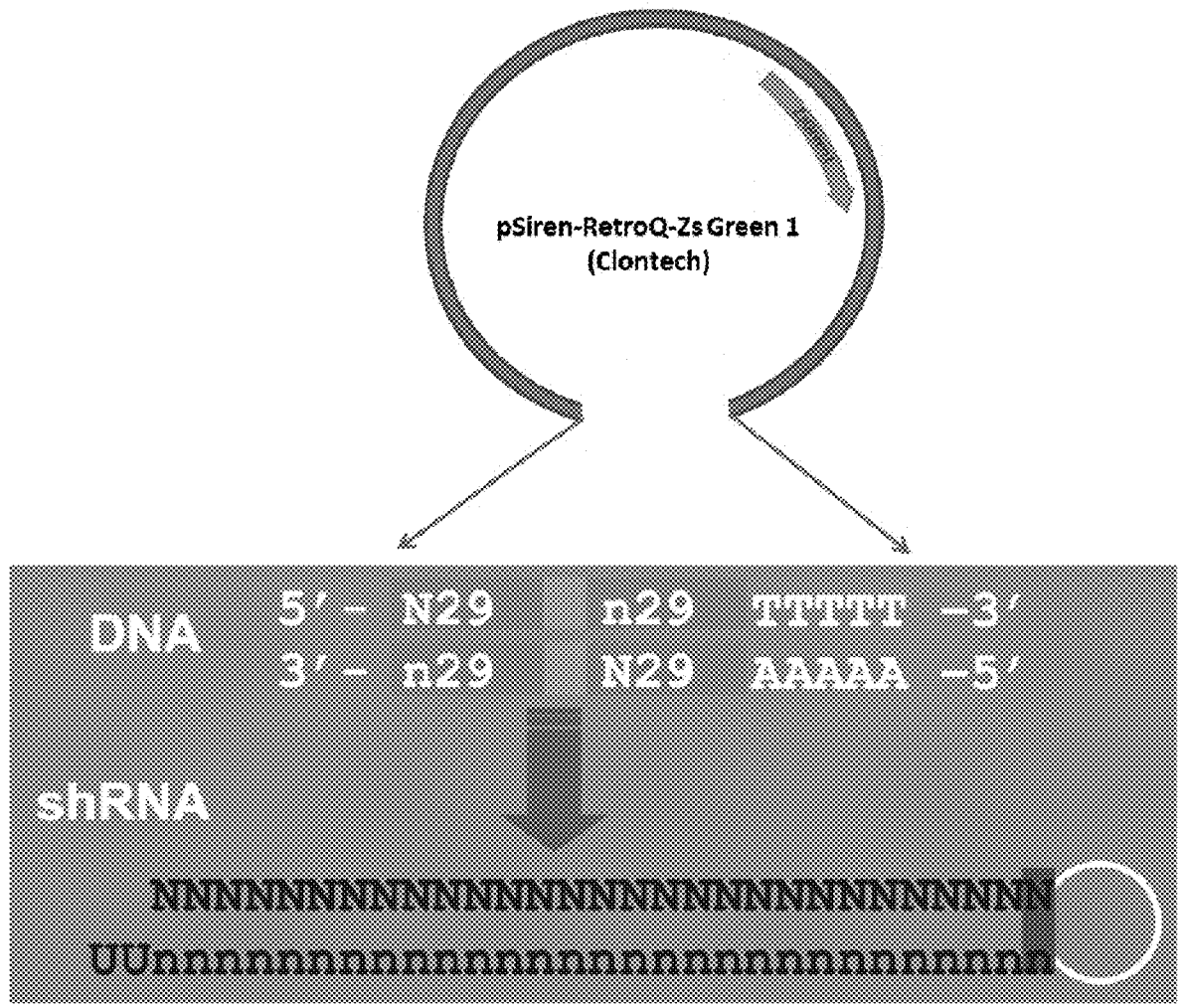
FIG. 2: To encode a random shRNA in a vector, a random DNA sequence (N29) and its reverse complement (n29) in the same DNA strand, separated by a non-complementary loop sequence was used.

The inherent complexity and unpredictability of small-RNA effects described above, and the implications for the problem of off-target effects in siRNA therapeutic initiatives, led to the design, synthesis, and validation of the first random, shRNA-expressing library. The design and synthesis were quite complex. Random DNA oligonucleotides (oligos) can be obtained from almost any oligo synthesis facility. The challenge was to create the reverse complement of each random oligo in the same DNA strand, separated by a non-complementary loop sequence, so as to encode a random shRNA (FIG. 2). The successful design, synthesis, and validation of a first-generation, 300,000-clone library is described (Wang et al., "A random shRNA-encoding library for phenotypic selection and hit-optimization," PLoS ONE 3 (9):e3171, 2008; and U.S. Published Appl. No. 2009/0285788, each of which is hereby incorporated by reference in its entirety).

The approach to what is called "positive selection" is as follows: First, the library is introduced into pooled cells, usually by infection after packaging as retroviruses. Second, cells with the desired phenotype are selected, by survival, by growth advantage, or by flow-sorting for appropriate markers. Third, the shRNA-encoding sequences that produced the desired phenotype are retrieved by polymerase chain reaction (PCR) and cloned back into the library vector. Fourth, the retrieved sequences are confirmed by testing them individually in cells. Fifth, effective sequences are optimized by random mutagenesis and re-screening.

This random approach is both functional and unbiased. The most effective shRNA sequences for a given application, will, at minimum, target many genes, and will likely exert their effects in unpredictable ways. In addition, just as there is no reason to assume that shRNA sequences designed to target single genes will be the most effective for any given therapeutic application, there is no reason to assume that such sequences will have the most favorable therapeutic indices. By using a random-sequence, shRNA-encoding library, and a functional approach, and by extending the cell-based screens over weeks to months, shRNA sequences are identified that are the most effective, and the least toxic, without prior assumptions.

The approach described above was validated by screening the first-generation library for shRNAs that protect an IL3-dependent cell line from IL3 withdrawal, and by optimizing one of the initial hits by random mutagenesis and re-screening. The library was then screened in a primary cell-culture model of Friedreich ataxia (FA).

The Friedreich's Ataxia (FA) Screen

Figure 3:
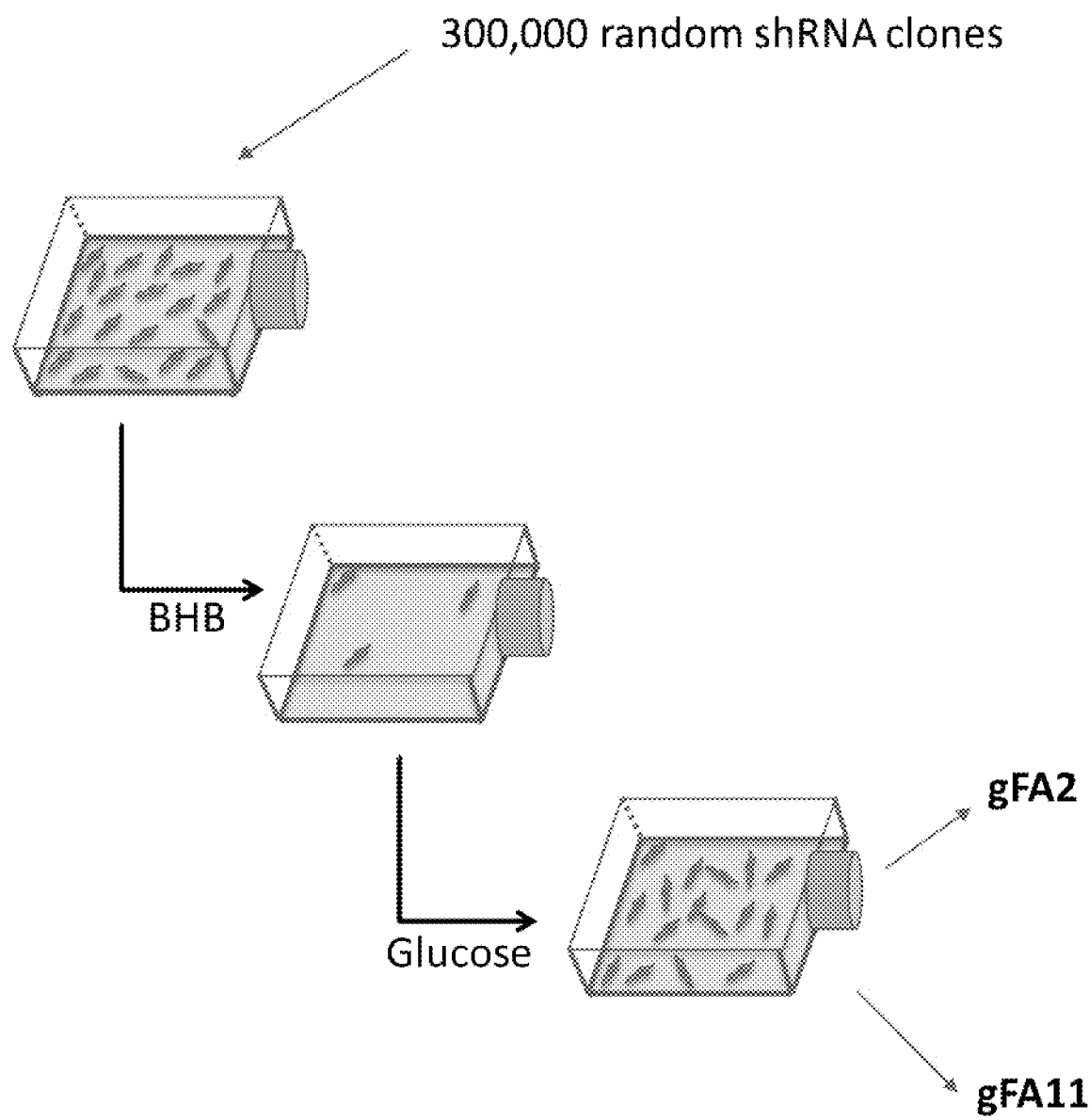
FIG. 3: Library screening. Primary Friedreich's ataxia (FA) fibroblasts (Coriell GM3816) were infected with a 300,000-clone, random shRNA library. Four days post-infection the cells were switched to DMEM containing 5 mM BHB. After two weeks, only 1% of the cells survived. The cells were then moved into DMEM with glucose for two weeks. The entire cycle was repeated two more times Finally, genomic DNA from the selected cells was extracted, the shRNA-expressing cassette by PCR was amplified, and cloned back into the parental vector. Two clones were highly represented and chosen for further analysis: gFA2 and gFA11.
Figure 4B:
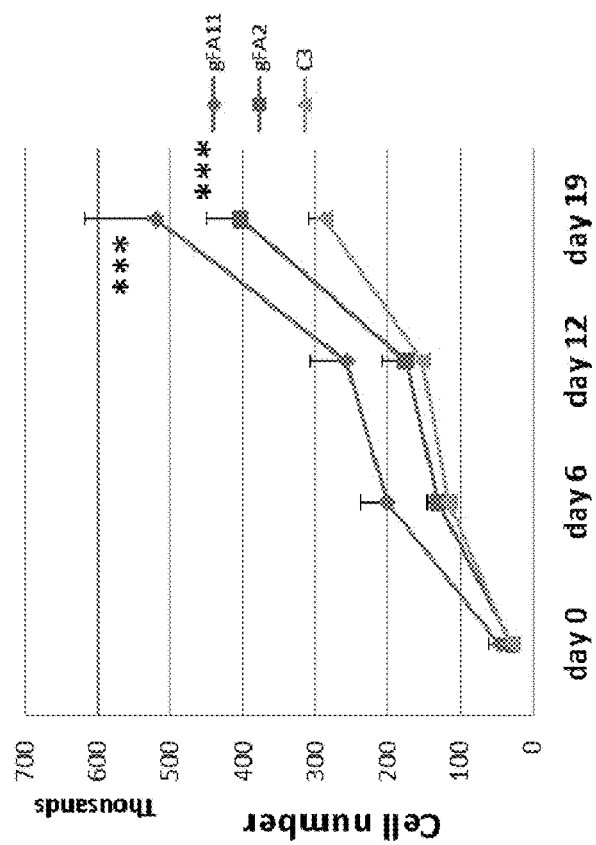
FIGS. 4A and 4B: Clones gFA2 and gFA11 increase the growth of FA fibroblasts. FA 3665B cells were infected with gFA2 (squares), gFA11 (diamonds) or a random clone (C3) (triangles). Cells were then sorted and GFP-positive cells were grown in DMEM plus BHB 5 mM (FIG. 4A) or in DMEM plus 5 mM glucose (FIG. 4B) ***=p value<0.05.
Figure 4A:
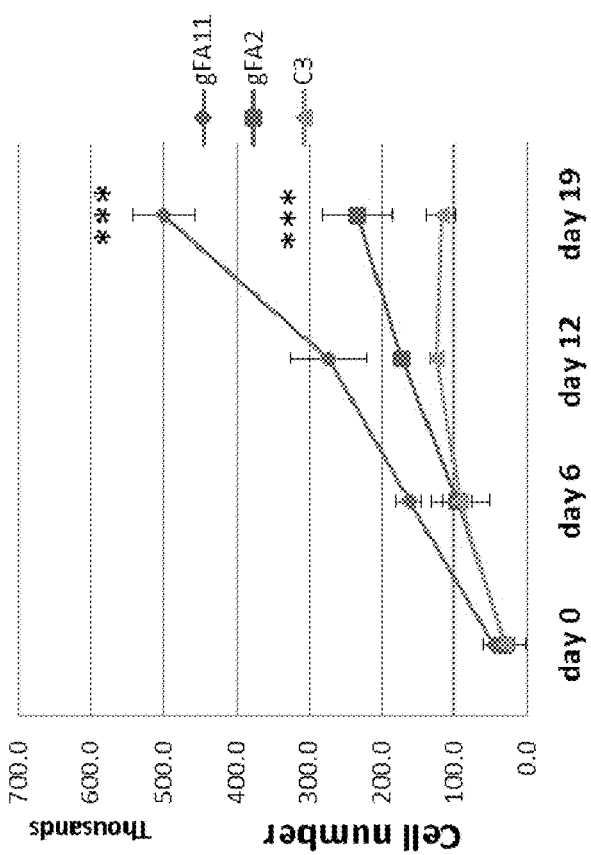

FA is caused by intronic trinucleotide repeat expansions that decrease expression of frataxin, a protein involved in mitochondrial iron-sulfur-cluster biogenesis. Clones were selected that reverse the slow-growth phenotype of primary FA fibroblasts in media with beta-hydroxybutyrate, a carbon source that particularly stresses cells with mitochondrial dysfunction (FIGS. 1 and 3). Among several clones identified, two clones have been tested and confirmed (FIG. 4): "Clone 2" (also referred to as gFA2) and "Clone 11" (also referred to as gFA11). The DNA coding strand for the shRNA sequences of those two books (gFA2 and gFA11) are provided below, with the loop-encoding sequences in brackets. The shRNAs themselves are RNA versions of these sequences, with T changed to U.

```
gFA2:
                                         (SEQ ID No: 1)
5'-GCCAATCGGGGAGGTCGGCGCATATCATG[CTAAAC]
CATGATATGCGCCGACCTCCCCGATTGGC-3' gFA11:
                                         (SEQ ID No: 2)
5'-CAACAGAATGGAAGAGTGCTGGGTGGTGG[CTAAAC]
CCACCACCCAGCACTCTTCCATTCTGTTG-3'
```

Figure 5B:
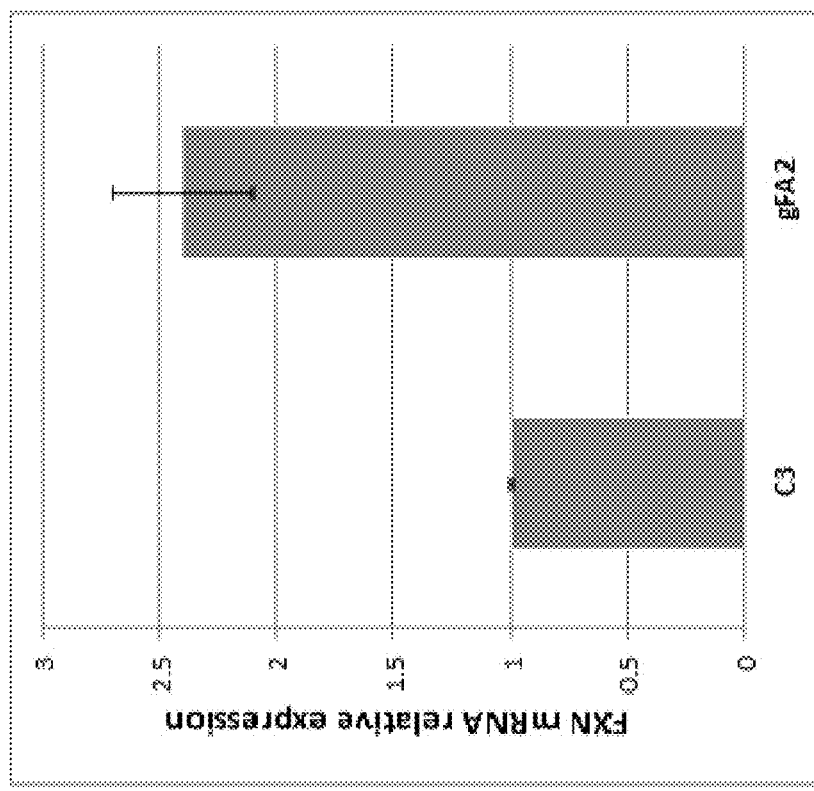
FIGS. 5A and 5B: gFA2 increases frataxin expression in FA fibroblasts as shRNA or siRNA. Frataxin expression in GM3816 cells infected with gFA2 vs. a random clone (C3) (FIG. 5A) and in GM3665B cells transfected with 10 nM gFA2 siRNA or a random clone (C3) (FIG. 5B). Cells were transfected every 3-4 days for two weeks and kept in BHB medium after the first transfection. ***=p value<0.005
Figure 5A:
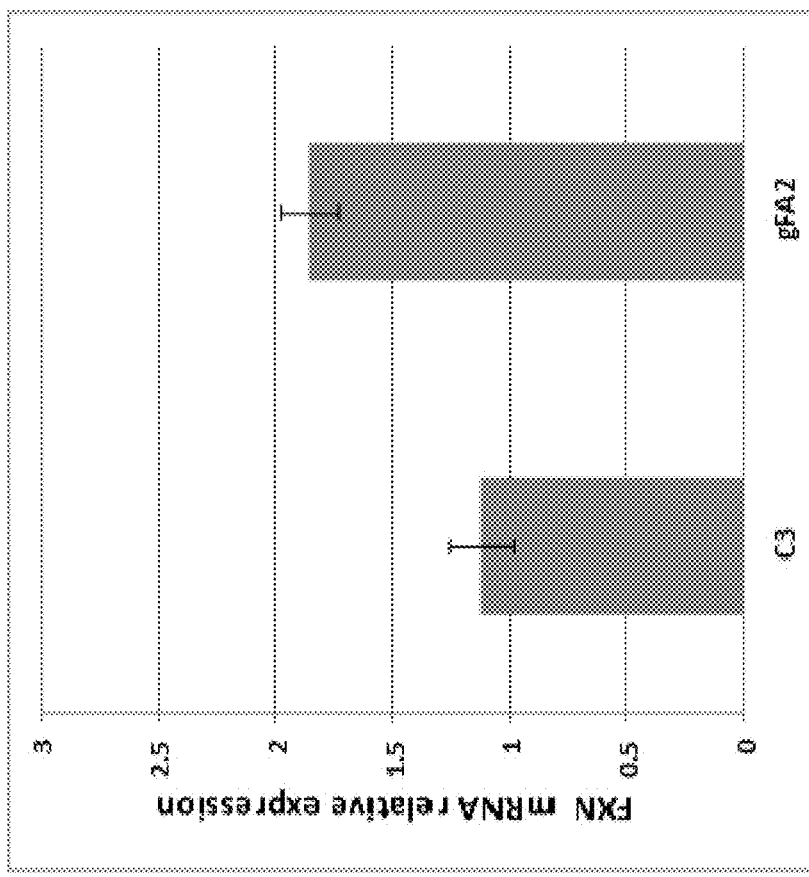
Figure 6:
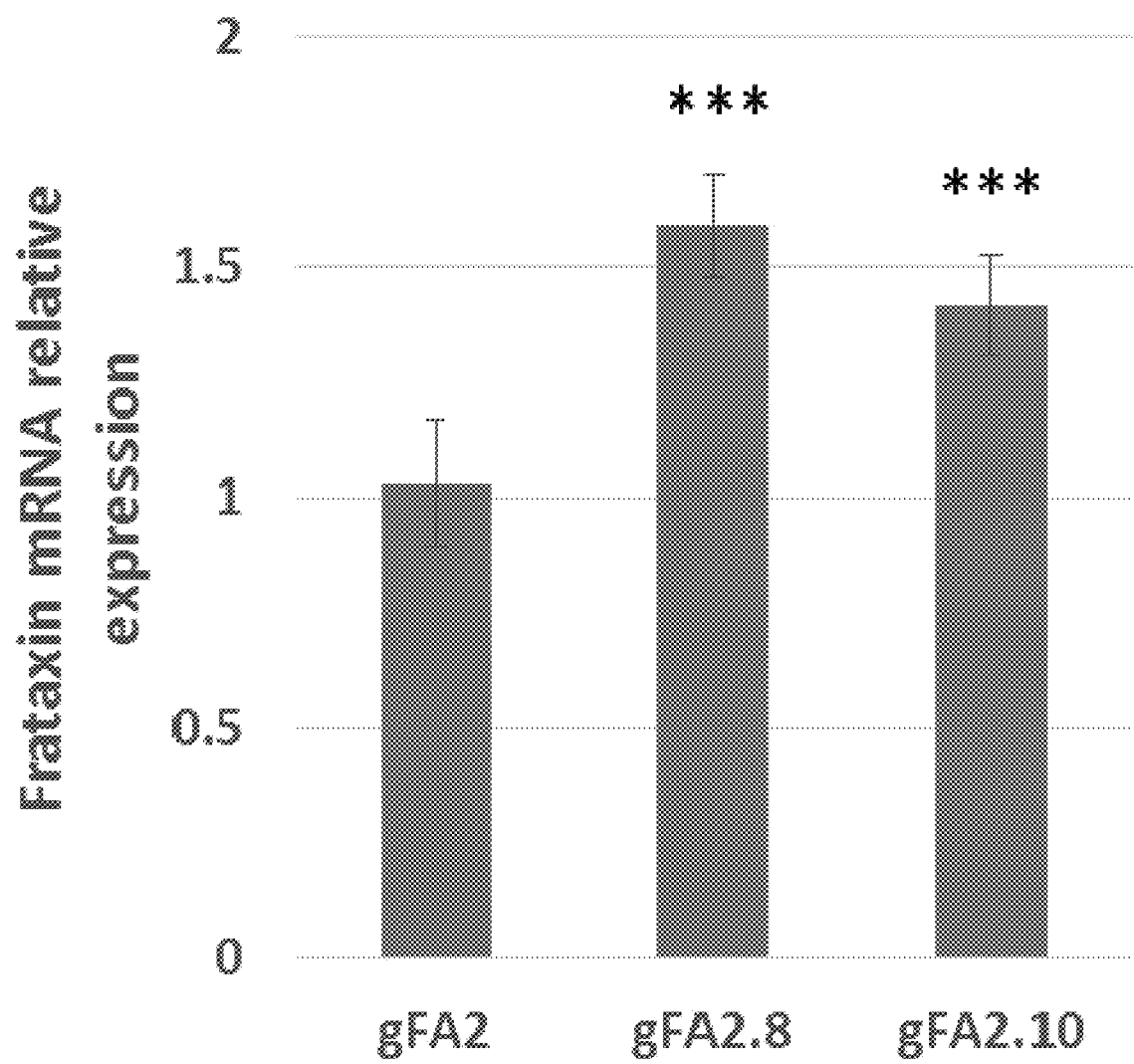
FIG. 6: Hit-optimization of clone gFA2. A sub-library of ~3000 sequences was constructed, each with a limited number of random mutations compared to gFA2. This sub-library was screened as described previously and two gFA2-variant clones, gFA2.8 and gFA2.10, were identified. Frataxin expression in primary FA fibroblasts (4675) transfected with 10 nM siRNA of each sequence demonstrates that clones gFA2.8 and gFA2.10 are more efficacious. (Cells were transfected every two days for one week and kept in DMEM plus 5 mM BHB after the first transfection. ***=p value<0.005). gFA2.8 has 5 mutations compared to gFA2; as a result, there are 5 mismatched bases in the hairpin structure.

As a vector-expressed shRNA, or as a transfected siRNA, Clone 2 partially reverses the decreased expression of frataxin that is the hallmark of the disorder (FIG. 5). Clone 2 was randomly mutagenized (to create a sub-library) and the Clone 2 sub-library was re-screened in FA cells (FIG. 6). Two gFA2-variant clones, gFA2.8 and gFA2.10, were identified. gFA2.8 has 5 mutations compared to gFA2; as a result, there are 5 mismatched bases in the hairpin structure as indicated below (differences between gFA2 and gFA2.8 are enlarged and in bold).

```
gFA2:
                                         (SEQ ID No: 1)
5'-GCCAATCGGGGAGGTCGGCGCATATCATG[CTAAAC]
CATGATATGCGCCGACCTCCCCGATTGGC-3' gFA2.8:
                                         (SEQ ID No: 9)
5'-GCCCCTCGGGCAGGTCGGCGAATATCATG[CTAAAC]
TATGATATGCGCCGACCTCCCCGATTGGC-3' gFA2.10:
                                         (SEQ ID No: 10)
5'-GCCCCTCGGGCAGGTCGGCGAATATCATG[CTAAAC]
TATGATATGCGCCGACCTTCCCGATTGGC-3'
```

The sequences of the siRNA version of the gFA11 siRNA ("B11 siRNA") used in this Example, as well as the sequences of two mutated versions of the B11 siRNA ("MUT 1" and "MUT 2") are shown below as well with the mutations shown enlarged and in bold

```
gFA11 siRNA
                                         (SEQ ID No: 3)
5'- AACAGAAUGGAAGAGUGCUGGGUdGdG-3'

(SEQ ID No: 4)
3'-UGUUGUCUUACCUUCUCACGACCCA C C-5' gFA11-Mut1 siRNA
                                         (SEQ ID No: 5)
5'- AACACAAUGGAAGAGUGCUGGGUdGdG-3'

(SEQ ID No: 6)
3'-UGUUGUGUUACCUUCUCACGACCCA C C-5' gFA11-Mut2 siRNA
                                         (SEQ ID No: 7)
5'- AACAGAAUGGAAGAGUCCUGGGUdGdG-3'

(SEQ ID No: 8)
3'-UGUUGUCUUACCUUCUCAGGACCCA C C-5'
```

Figure 7:
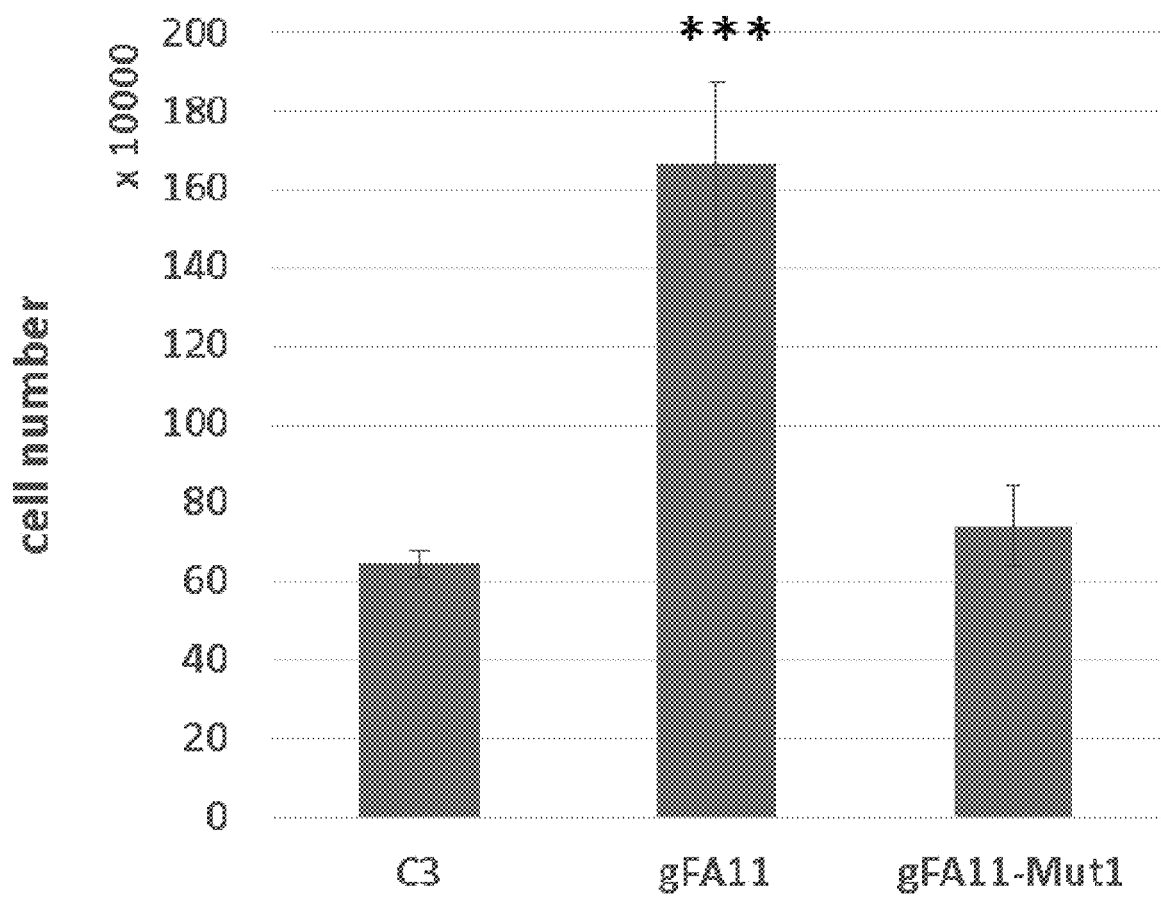
FIG. 7 shows that the growth-enhancing effect of gFA11 in human fibroblast GM3816 cells treated with gFA11 siRNA is diminished with a mutation in the seed sequence (gFA11-Mut1) but not with a mutation in the non-seed sequence (data not shown). ***p<0.005.

The siRNA version of the gFA11 sequence was used and shown to recapitulate the phenotype induced by the corresponding shRNA sequence in the human FA fibroblasts (See FIG. 7). As discussed above, important sequences in siRNAs and shRNAs are the "seed" sequences, which are usually nucleotides 2 through 7 (or so) at the 5' end of the guide strand. Thus, gFA11-Mut1 should change the seed sequence of gFA11 for the upper strand, but not for the lower strand, while gFA11-Mut2 should change the seed sequence for the lower strand, but not for the upper strand. FIG. 7 shows that with gFA11-Mut1, the growth-enhancement phenotype of gFA11 is affected, but not with gFA11-Mut2 (data not shown), which implicates the upper strand (SEQ ID No: 3) as the gFA11 guide strand for growth enhancement.

Figure 8A:
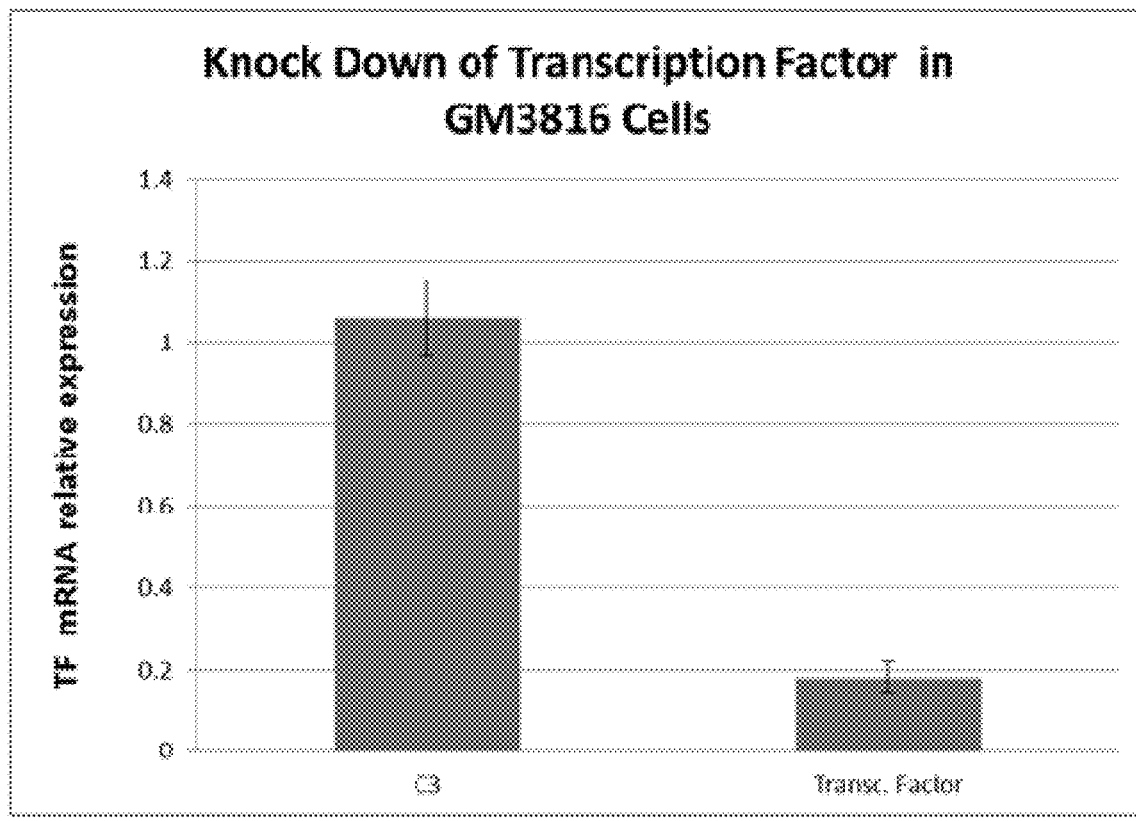
FIGS. 8A and 8B: Microarray analysis of GM3816 cells infected with gFA11 vs. cells infected with the Mut1 siRNA was performed. Ingenuity Pathway Analysis (IPA) of the microarray data identified a transcription factor as a negative upstream regulator (activation z-score of −4.26). This transcription factor was knocked down using a directed siRNA and recapitulated the growth phenotype seen with gFA11 (GM3816 were transfected with 10 nM siRNA every 3-4 days for one week).
Figure 8B:
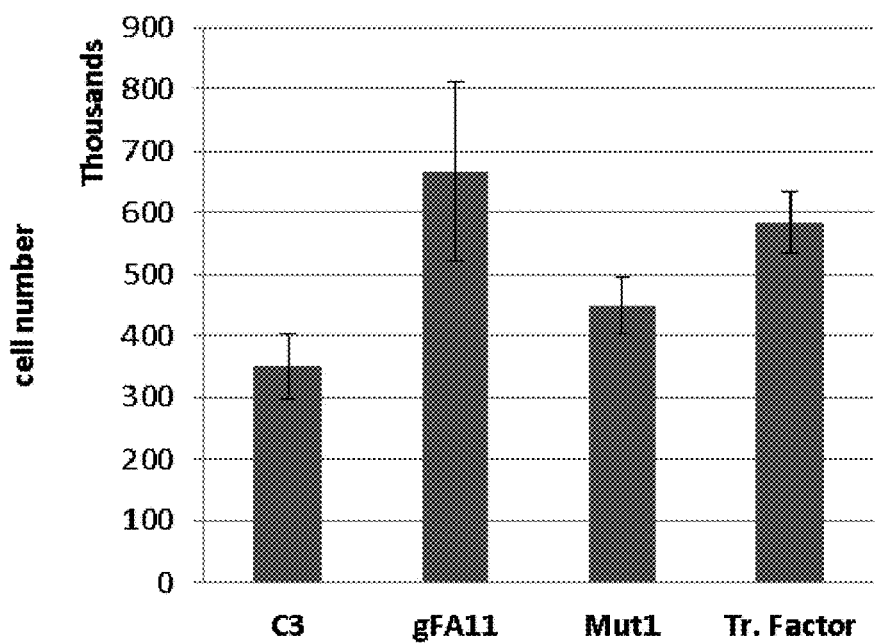
Figure 9A:
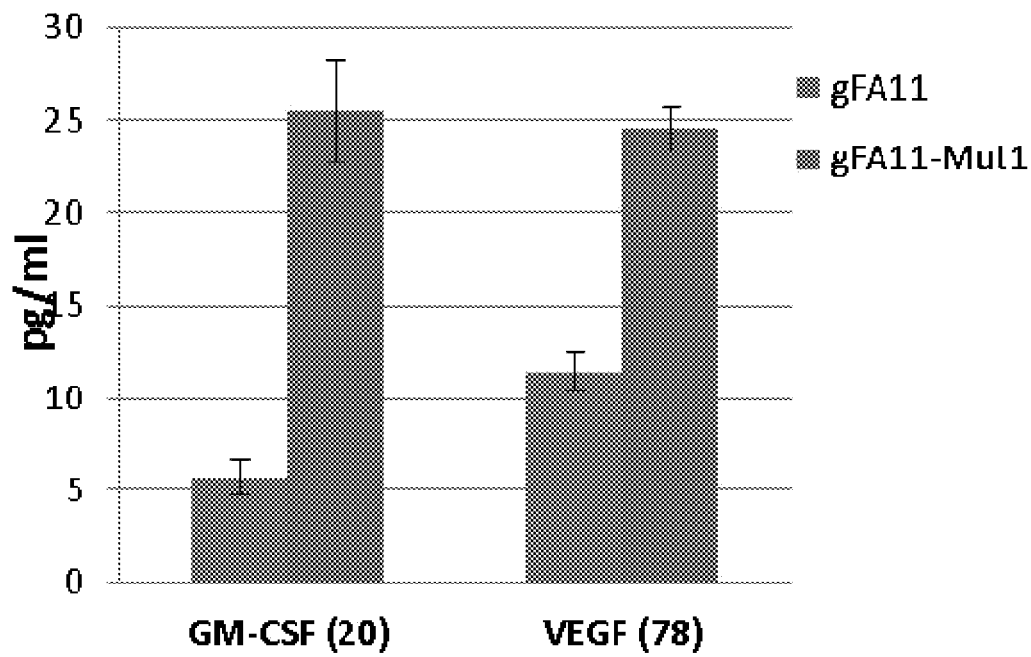
FIGS. 9A and 9B show the effect of gFA11 and gFA11-Mut1 shRNA sequences on the secretion of cytokines as measured by ELISA.
Figure 9B:
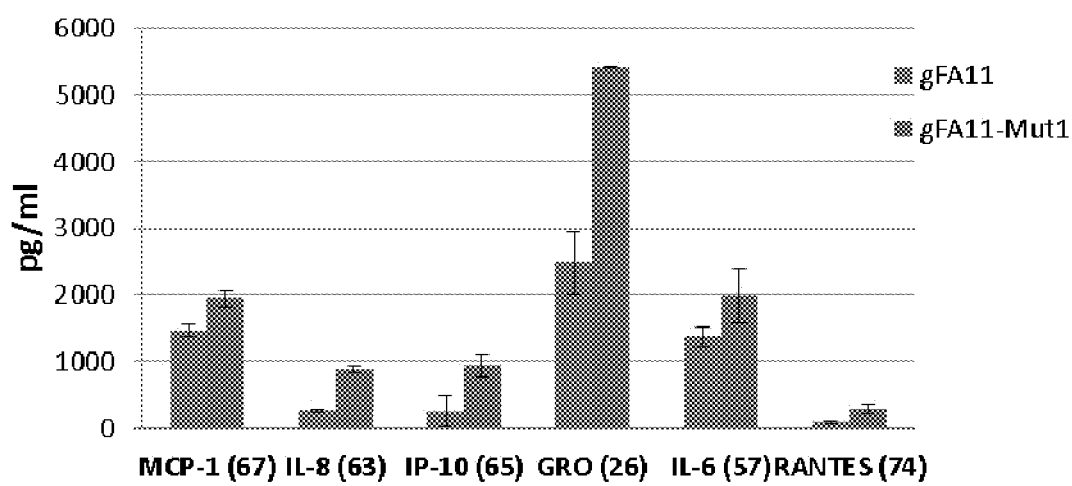
Figure 10:
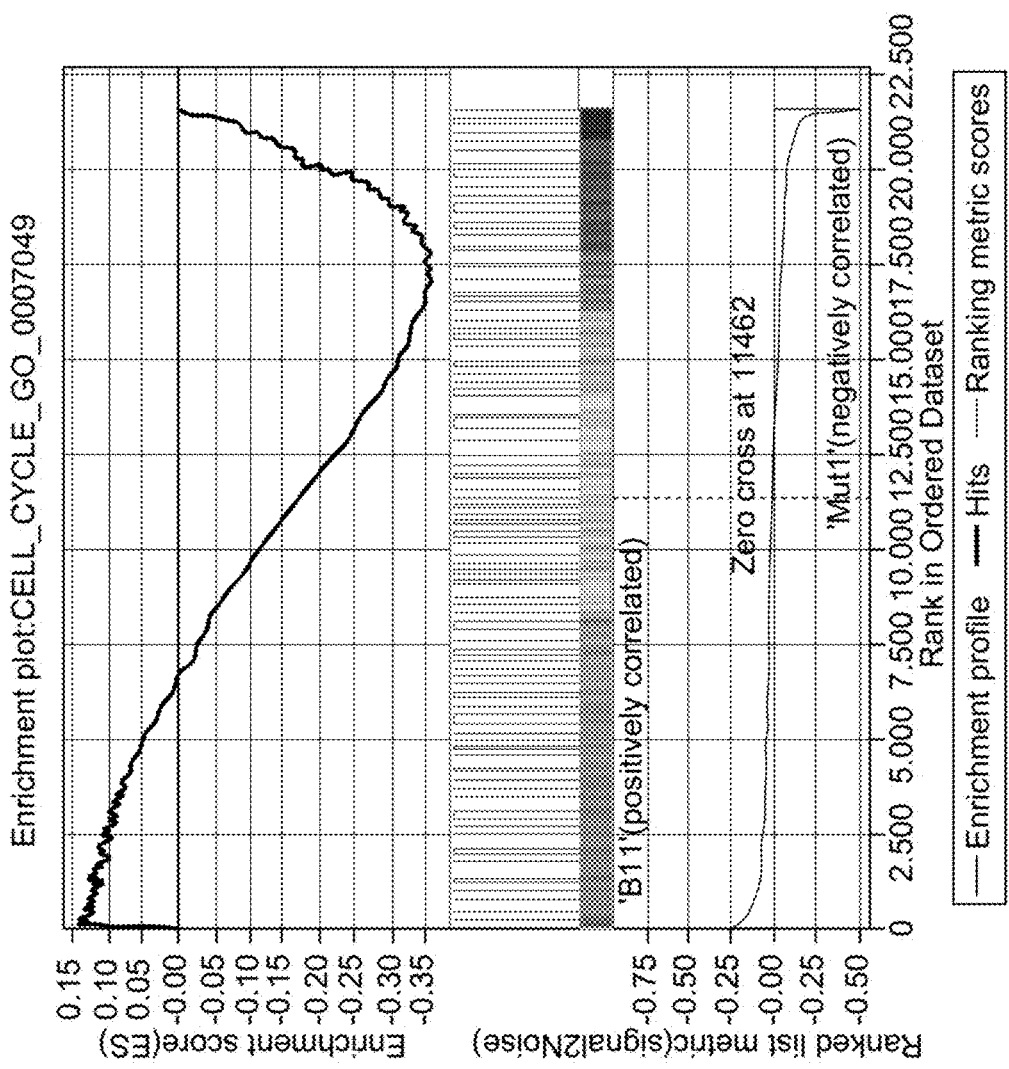
FIG. 10: Gene Set Enrichment (G.S.E.) analysis of microarray data.
Figure 10:
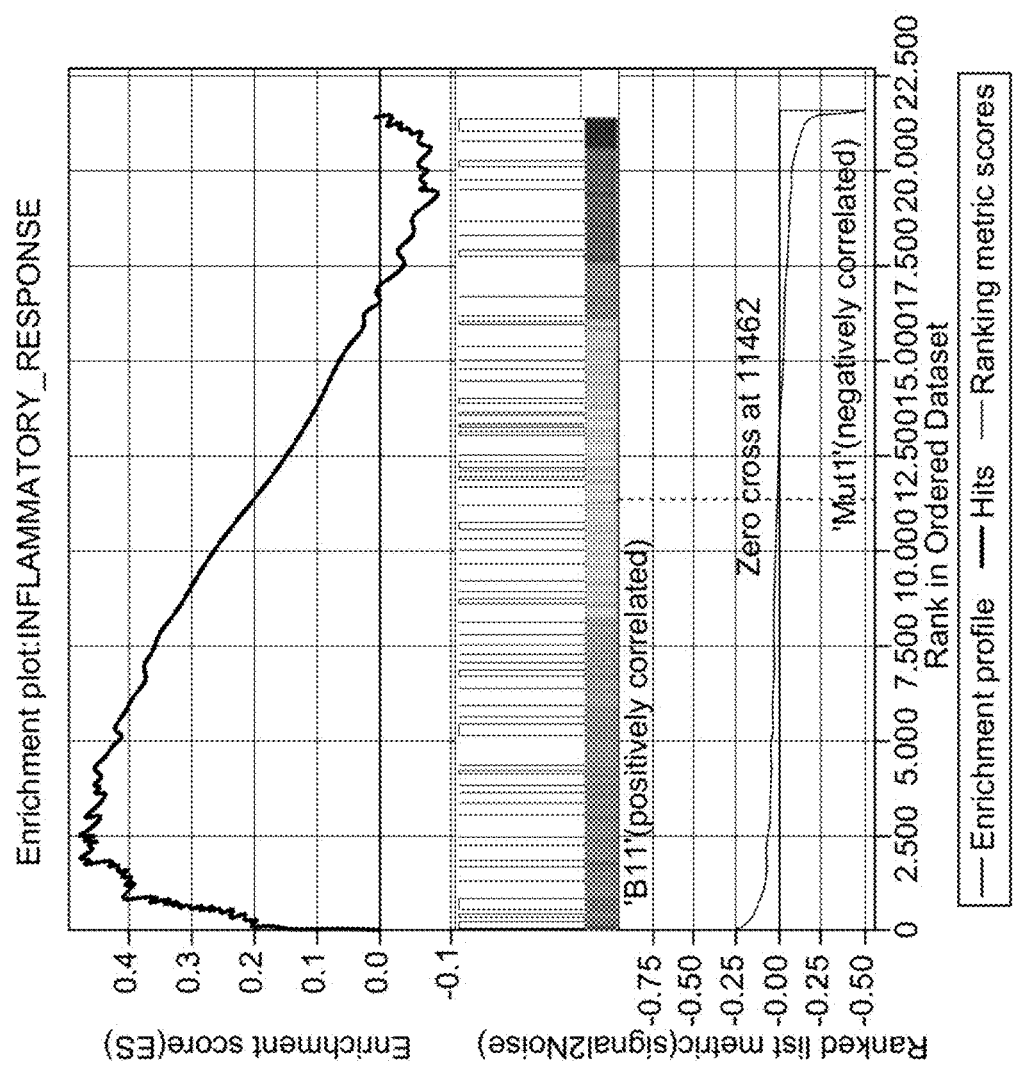
Figure 10:
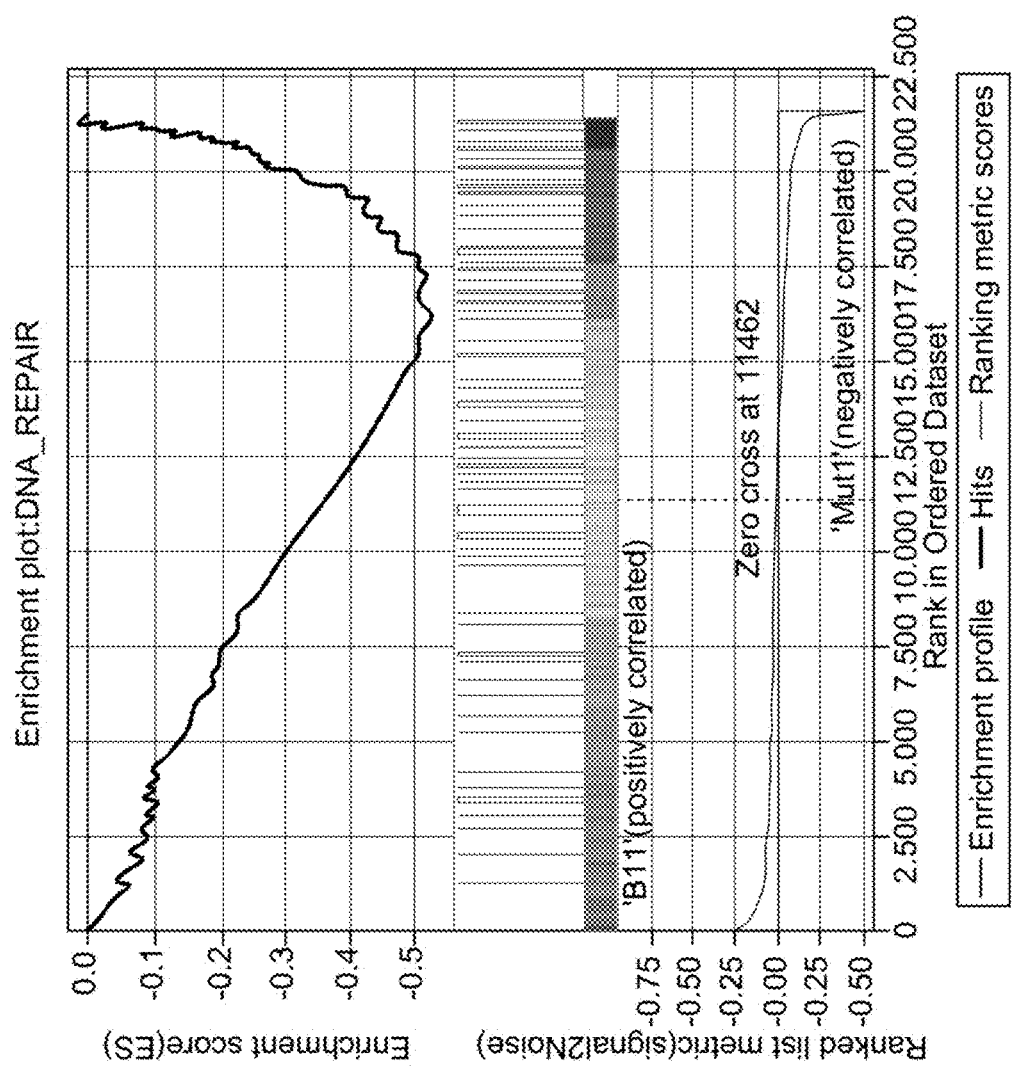
Figure 11A:
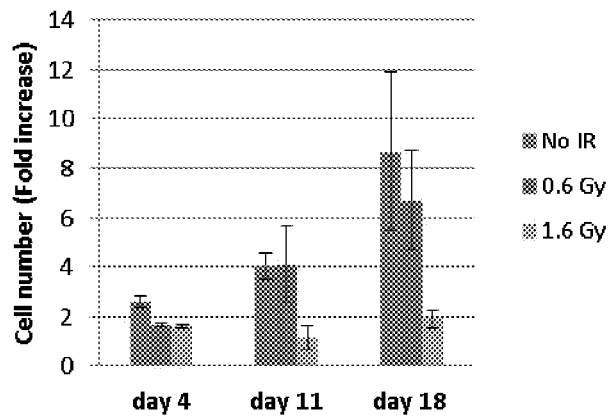
FIGS. 11A and 11B: FA cells are sensitive to ionizing radiation dose-dependent sensitivity of GM3816 cells (FIG. 11A, top); Cells transfected with gFA11 undergo growth arrest following 0.6 Gy irradiation but are able to recover as opposed to cells transfected with Mut1 or a control clone (FIG. 11B, below).
Figure 11B:
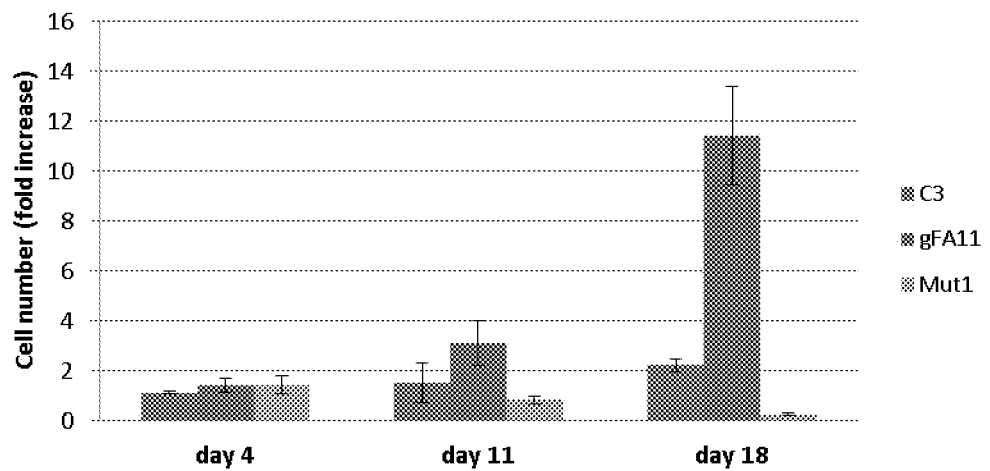

To understand the function of Clone 11 (which does not increase frataxin expression, but which is more effective than Clone 2 in reversing the slow-growth phenotype of primary FA fibroblasts in media with beta-hydroxybutyrate), microarray analyses of FA cells expressing Clone 11 (FIGS. 7, 8 and 10) were performed. As a control, FA cells expressing a version of Clone 11 rendered inactive by a point mutation in the seed sequence (i.e., gFA11-Mut1) were used. Using the Database for Annotation, Visualization and Integrated Discovery (DAVID), it was found that the gene-expression profile induced by Clone 11 in FA cells included significantly down-regulated genes involved in cytokine secretion. The media of FA cells expressing Clone 11 were tested and were found to demonstrate statistically significant decreases in IL6 (IL-6) ($p=0.09$), IL8 (IL-8) ($p=0.001$), GM-CSF ($p<0.001$), RANTES ($p=0.04$), and IL1-beta (IL-1-beta) ($p=0.01$) (See FIG. 9). Additional decreases were seen in VEGF ($p<0.001$), MCP-1 ($p=0.005$), IP-10 ($p=0.01$), and GRO ($p=0.003$). (These data are two-sided p-values. If one considers one-sided p-values, due to an expectation of reduction, then IL-6 becomes significant at $p=0.09/2=0.045$.) This pattern of cytokine secretion suggests a reversal of a senescence-associated secretion phenotype. Of relevance, it has been shown that silencing of the FA disease gene induces a senescence phenotype. Also of relevance, it has been shown that silencing of the FA disease gene in human astrocytes triggers cell death and the release of factors that cause neuronal toxicity, suggesting that, as in other neurodegenerative disorders, changes in non-neuronal cells might contribute to the pathogenesis of FA, and that Clone 11 might ameliorate the effects of these changes. Finally, gene-expression analyses of cells expressing Clone 11 also indicated an up-regulation of genes involved in DNA repair. Given that certain DNA repair enzymes, such as XPD and FancJ, are known to contain iron-sulfur clusters, the effects of expressing Clone 11 on cell susceptibility to gamma irradiation were tested, and it was found that expression of Clone 11 is protective (FIG. 11).

Example 1: Target Pathway for the Treatment of Friedreich's Ataxia and SB-203580

Figure 12:
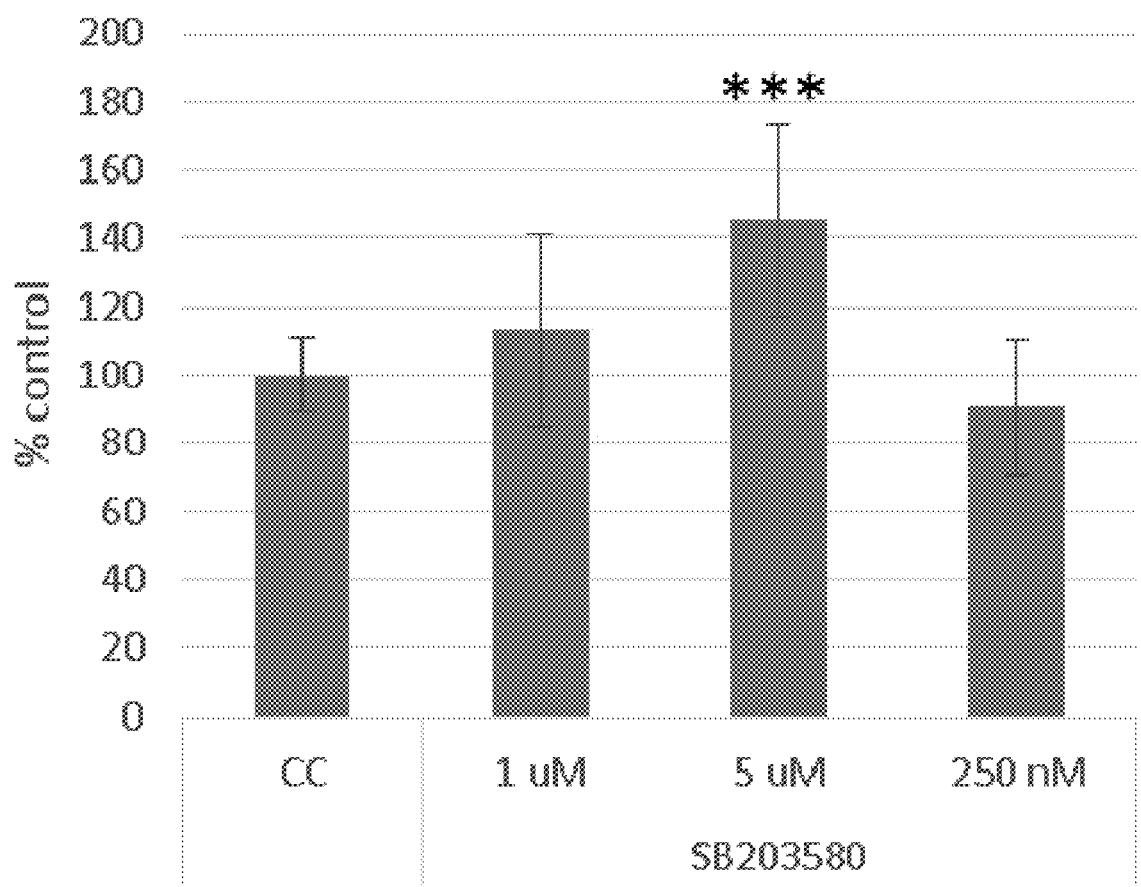
FIG. 12: SB203580, a p38 MAP kinase inhibitor, had an activation z-score of +3.14. This drug was tested at different concentrations and found to increase the growth of FA cells in a dose-dependent manner (Cells were treated with the drug or carrier control (DMSO) every 48 h for two weeks.) ***p<0.005.

Using the Ingenuity software package, it was found that the gene-expression profile induced by Clone 11 in FA cells is remarkably similar to that induced by the drug SB-203580 (with a z score of 3.18), and to that induced by inhibition of the transcription factor NupR1 (with a z score of 4.15). Treatment of FA cells with SB-203580, or with a transfected siRNA targeted to NupR1, recapitulates the phenotype induced by Clone 11, namely reversal of the slow-growth phenotype in beta-hydroxybutyrate-based media (FIG. 12). These experiments have been repeated several times, over 4 days, 7 days, and 10 days, with the same results. Therefore, random shRNA screening can be combined with bioinformatic pattern matching to identify conventional chemical-compound therapeutic candidates, and potential therapeutic target proteins.

SB-203580 is an inhibitor of the MAP kinase, p38. It has been shown that the p38 pathway regulates iron-sulfur-cluster assembly through the phosphorylation of MK2, which in turn phosphorylates IscU, a component of the iron-sulfur-cluster assembly complex (Tian, L. et al., *J Biol Chem* 289, 31856-65 (2014)). A mutation in IscU can bypass the need for frataxin (Yoon, H. et al., *Biochem J* 441, 473-80 (2012); Yoon, H. et al., *Biochem J* 459, 71-81 (2014)) by allowing frataxin-independent activation of the cysteine desulfurase that mobilizes sulfur for iron-sulfur-cluster assembly (Pandey, A. et al., *J Biol Chem* 288, 36773-86 (2013)). These results have uncovered a pathway that modulates IscU, demonstrate that the need for frataxin has been bypassed, and that specific inhibition of p38 (or MK2) is useful as a therapeutic strategy for the treatment of FA.

Figure 13:
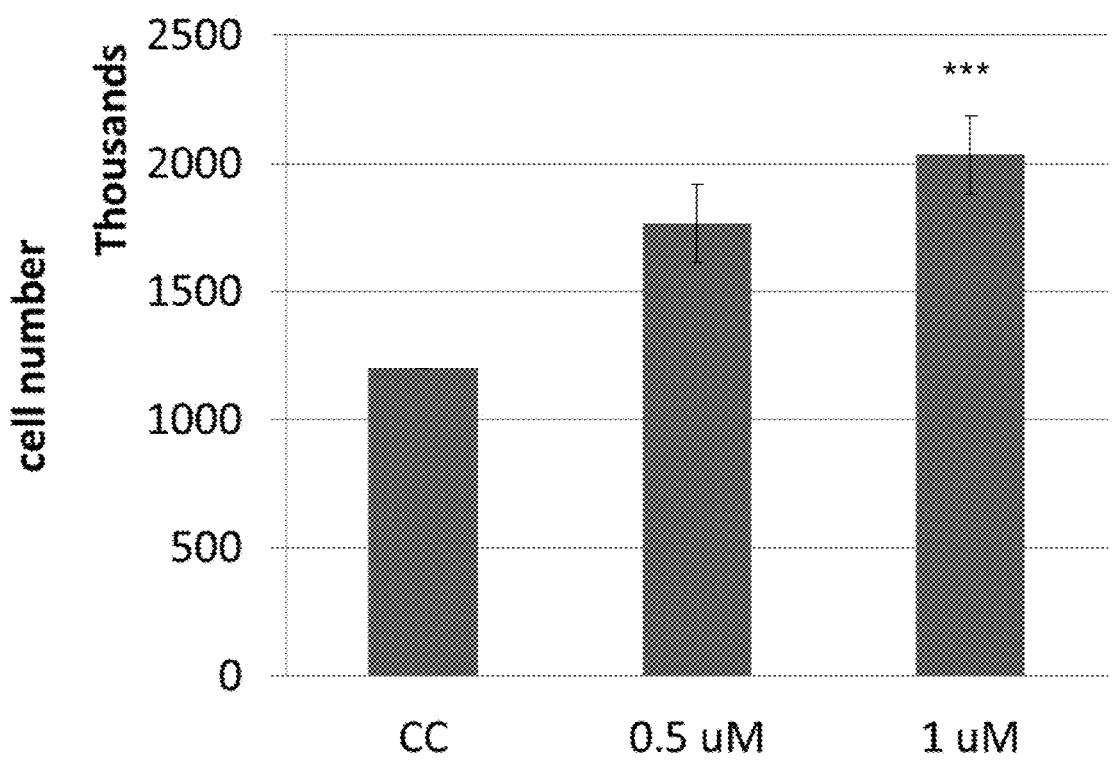
FIG. 13: SB-203580 reverses the growth defect of primary FA fibroblasts in mitochondrial stress medium.

As shown in FIG. 13, SB-203580 reverses the growth defect of primary FA fibroblasts in mitochondrial stress medium.

Example 2: Additional p38 MAPK Inhibitors Reverse the Growth Defect of Primary FA Fibroblasts Consistent with this hypothesis, treatment of FA cells with four additional inhibitors of p38, VX-702 and LY-2228820 (both in Phase II trials for Rheumatoid Arthritis), and SB-202190 and BIRB-796, also recapitulate the phenotype induced by Clone 11.

Figure 14:
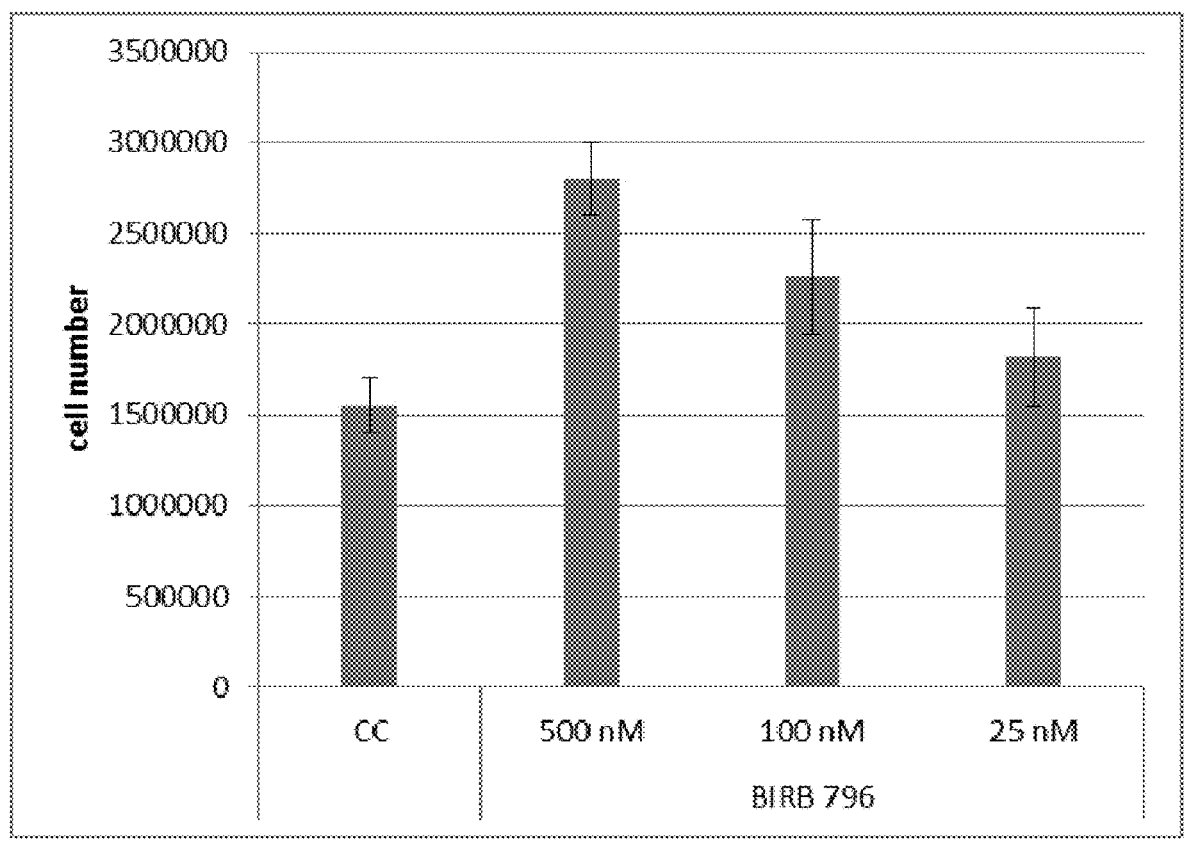
FIG. 14: BIRB-796, another p38 MAP kinase inhibitor, also reverses the growth defect of primary FA fibroblasts.

As shown in FIG. 14, BIRB-796 (doramapimod) also reverses the growth defect of primary FA fibroblasts.

As with the results for SB-203580 and BIRB-796, analogous experiments have also shown a reversal of the growth defect of primary FA fibroblasts by GW-856553 (GW856553X; losmapimod), PH-797804, LY-2228820 (ralimetinib dimesylate), SB-202190 (FHPI), ARRY-614 (pexmetinib), VX-702, and VX-745. FIGS. 15A-15D show the results of studies of the effectiveness of additional p38 MAPK inhibitors (PH 79 [PH-797804]; ARRY 614 [ARRY-614; pexmetinib]; LSP [losmapimod; GW856553]; and SB-202190) on the growth defect of primary FA fibroblasts. In addition, LY-2228820 at 50 nM increased growth 1.6 fold ($p<0.005$); VX-702 at 500 nM increased growth 1.2 fold ($p=0.02$).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for treating a subject at risk for developing Friedreich's ataxia or suffering from Friedreich's ataxia or reducing the symptoms thereof comprising administering to the subject a therapeutically effective amount of a p38 mitogen-activated protein kinase (MAPK) inhibitor or a pharmaceutical composition thereof, wherein the p38 MAPK inhibitor is selected from the group consisting of ARRY-371797, ARRY-614 (pexmetinib), AZD-7624, LY-2228820 (ralimetinib dimesylate), LY-3007113, FX005, GSK610677, GW856553 (losmapimod), SB-681323 (dilmapimod), KC706, UR-13870, PF-03715455, VX-745, SCIO-469 (talmapimod), PH-797804, VX-702, SB-202190 (FHPI), SB-239063, BIRB-796 (doramapimod), BMS-582949, pamapimod, and pharmaceutically acceptable derivatives thereof.

2. The method according to claim 1, wherein the inhibitor is administered in combination with one or more additional p38 MAPK inhibitors.

3. The method according to claim 1, wherein the subject is a human.

4. The method according to claim 1, further comprising the step of administering an additional agent for treating the subject.

5. A method for compensating for a frataxin deficiency or mutation in a subject comprising administering to the subject a therapeutically effective amount of a p38 mitogen-activated protein kinase (MAPK) inhibitor or a pharmaceutical composition thereof, wherein the p38 MAPK inhibitor is selected from the group consisting of ARRY-371797, ARRY-614 (pexmetinib), AZD-7624, LY-2228820 (ralimetinib dimesylate), LY-3007113, FX005, GSK610677, GW856553 (losmapimod), SB-681323 (dilmapimod), KC706, UR-13870, PF-03715455, VX-745, SCIO-469 (talmapimod), PH-797804, VX-702, SB-202190 (FHPI), SB-239063, BIRB-796 (doramapimod), BMS-582949, pamapimod, and pharmaceutically acceptable derivatives thereof.

6. The method according to claim 5, wherein the inhibitor is administered in combination with one or more additional p38 MAPK inhibitors.

7. The method according to claim 5, wherein the subject is a human.

8. The method according to claim 5, further comprising the step of administering an additional agent for treating the subject.

9. A method for compensating for a frataxin deficiency or mutation in a primary fibroblast cell comprising administering to the primary fibroblast cell an effective amount of a p38 mitogen-activated protein kinase (MAPK) inhibitor, wherein the p38 MAPK inhibitor is selected from the group consisting of ARRY-371797, ARRY-614 (pexmetinib), AZD-7624, LY-2228820 (ralimetinib dimesylate), LY-3007113, FX005, GSK610677, GW856553 (losmapimod), SB-681323 (dilmapimod), KC706, UR-13870, PF-03715455, VX-745, SCIO-469 (talmapimod), PH-797804, VX-702, SB-202190 (FHPI), SB-239063, BIRB-796 (doramapimod), BMS-582949, pamapimod, and pharmaceutically acceptable derivatives thereof.

10. The method according to claim 9, wherein administering to the cell comprises administering to the cell in vitro, in vivo, or ex vivo.

11. The method according to claim 1, wherein the pharmaceutical composition further comprises a pharmaceutically acceptable carrier or diluent, a binder, or a preservative.

12. The method according to claim 5, wherein the pharmaceutical composition further comprises a pharmaceutically acceptable carrier or diluent, a binder, or a preservative.

13. A method for increasing frataxin gene expression or a phenotype thereof in a cell having a frataxin deficiency or mutation, the method comprising administering to the cell an effective amount of a p38 mitogen-activated protein kinase (MAPK) inhibitor or a pharmaceutically acceptable derivative thereof, wherein the p38 MAPK inhibitor is selected from the group consisting of ARRY-371797, ARRY-614 (pexmetinib), AZD-7624, LY-2228820 (ralimetinib dimesylate), LY-3007113, FX005, GSK610677, GW856553 (losmapimod), SB-681323 (dilmapimod), KC706, UR-13870, PF-03715455, VX-745, SCIO-469 (talmapimod), PH-797804, VX-702, SB-202190 (FHPI), SB-239063, BIRB-796 (doramapimod), BMS-582949, pamapimod, and pharmaceutically acceptable derivatives thereof.

14. The method according to claim 13, further comprising decreasing the level of oxidative stress, decreasing the level of mitochondrial iron, and/or increasing the level of mitochondrial production of adenosine triphosphate (ATP) in the cell.

15. The method according to claim 13, wherein administering to the cell comprises administering to the cell in vitro, in vivo, or ex vivo.

16. A method for altering cytokine expression or secretion in a cell having a frataxin deficiency or mutation, the method comprising administering to the cell an effective amount of a p38 mitogen-activated protein kinase (MAPK) inhibitor or a pharmaceutically acceptable derivative thereof, wherein the p38 MAPK inhibitor is selected from the group consisting of ARRY-371797, ARRY-614 (pexmetinib), AZD-7624, LY-2228820 (ralimetinib dimesylate), LY-3007113, FX005, GSK610677, GW856553 (losmapimod), SB-681323 (dilmapimod), KC706, UR-13870, PF-03715455, VX-745, SCIO-469 (talmapimod), PH-797804, VX-702, SB-202190 (FHPI), SB-239063, BIRB-796 (doramapimod), BMS-582949, pamapimod, and pharmaceutically acceptable derivatives thereof.

17. The method according to claim 16, further comprising decreasing cytokine expression or secretion, wherein the cytokine is in the group consisting of IL6 (IL-6), IL8 (IL-8), GM-CSF, RANTES, IL1-beta (IL-1-beta), VEGF, MCP-1, IP10 (IP-10), and GRO.

18. The method according to claim 16, wherein administering to the cell comprises administering to the cell in vitro, in vivo, or ex vivo.

\* \* \* \* \*